United States Patent
Milne et al.

(10) Patent No.: US 6,608,120 B1
(45) Date of Patent: Aug. 19, 2003

(54) DIALLYLAMINE MONOMERS AND NETWORK POLYMERS OBTAINED THEREFROM

(75) Inventors: Paul E Milne, Malvern (GB); Keith M Blackwood, Bracknell (GB); Steven M Kelly, Hull (GB); Alan W Hall, Hull (GB); John W Goodby, Hull (GB)

(73) Assignee: Qinetiq Limited, London (GB)

( * ) Notice: Subject to any disclaimer, the term of this patent is extended or adjusted under 35 U.S.C. 154(b) by 0 days.

(21) Appl. No.: 09/743,896

(22) PCT Filed: Jul. 26, 1999

(86) PCT No.: PCT/GB99/02416

§ 371 (c)(1),
(2), (4) Date: Jan. 17, 2001

(87) PCT Pub. No.: WO00/06533

PCT Pub. Date: Feb. 10, 2000

(30) Foreign Application Priority Data

Jul. 25, 1998 (GB) ................................................ 9816171

(51) Int. Cl.[7] ..................... C07C 235/00; C07C 211/00; C07C 317/00; C08F 2/46; C08F 9/00

(52) U.S. Cl. ..................... 522/171; 522/173; 522/178; 522/182; 522/181; 522/180; 526/239; 526/274; 526/277; 526/278; 526/286; 526/288; 526/298; 526/310; 526/312; 568/1; 568/3; 568/8; 568/10; 568/14; 568/27; 568/28; 564/82; 564/463; 564/505; 564/509; 560/25; 560/48

(58) Field of Search ................................ 522/173, 176, 522/182, 183, 180, 90, 100, 104, 99, 151, 152, 153, 154, 171, 172; 526/239, 286, 288, 298, 274, 277, 278, 310, 312; 560/25, 48; 564/82, 463, 505, 509; 568/1, 3, 8, 10, 14, 27, 28

(56) References Cited

U.S. PATENT DOCUMENTS

| | | | |
|---|---|---|---|
| 3,256,220 A | | 6/1966 | Brotherton |
| 3,888,928 A | * | 6/1975 | Willis et al. ........... 204/157.64 |
| 3,912,693 A | * | 10/1975 | Shimizu et al. ............... 522/14 |
| 3,915,825 A | * | 10/1975 | Dighe et al. ................ 428/458 |
| 3,957,699 A | | 5/1976 | Solomon |
| 3,959,366 A | * | 5/1976 | Dighe et al. ................ 562/831 |
| 4,056,524 A | | 11/1977 | Walker |
| 4,121,986 A | | 10/1978 | Battaerd |
| 4,988,753 A | | 1/1991 | Rullmann et al. |
| 5,487,948 A | | 1/1996 | Stein |

FOREIGN PATENT DOCUMENTS

| | | |
|---|---|---|
| EP | 0 969 028 A2 | 1/2000 |
| EP | 0 969 061 A2 | 1/2000 |
| EP | 0970 946 A2 | 1/2000 |

OTHER PUBLICATIONS

G. B. Butler et al, "Preparation and polymerization of unsaturated Quaternary Ammonium Compounds, VII, Derivatives of 1,x–diamino–alkanes", Journal of the American Chemical Society, vol. 78, 1956, pp. 4797–4800.

R. A. Gossage et al, "Synthesis of a key reactive unit for use in the divergent or convergent synthesis of carbosilane dendrimers" Tetrahedron Letters, vol. 39, Apr. 16, 1998, pp. 2397–2400.

N. V. Usakov et al, "Synthesis of silicon carbon spiranes of metasthesis on an aluminum–rhenium catalyst", Bulletin of the Academy of Sciences of the USSR, Division of Chemical Science, (Engl. Trans.), vol. 38, No. 12, 1988, pp. 2561–2567.

* cited by examiner

Primary Examiner—Susan W. Berman
(74) Attorney, Agent, or Firm—Nixon & Vanderhye P.C.

(57) ABSTRACT

Compounds of the formula:

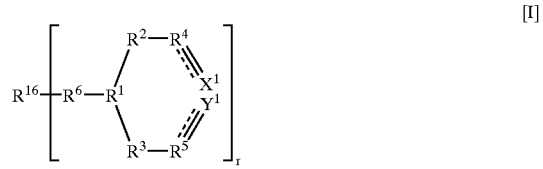

[I]

Figure 1:
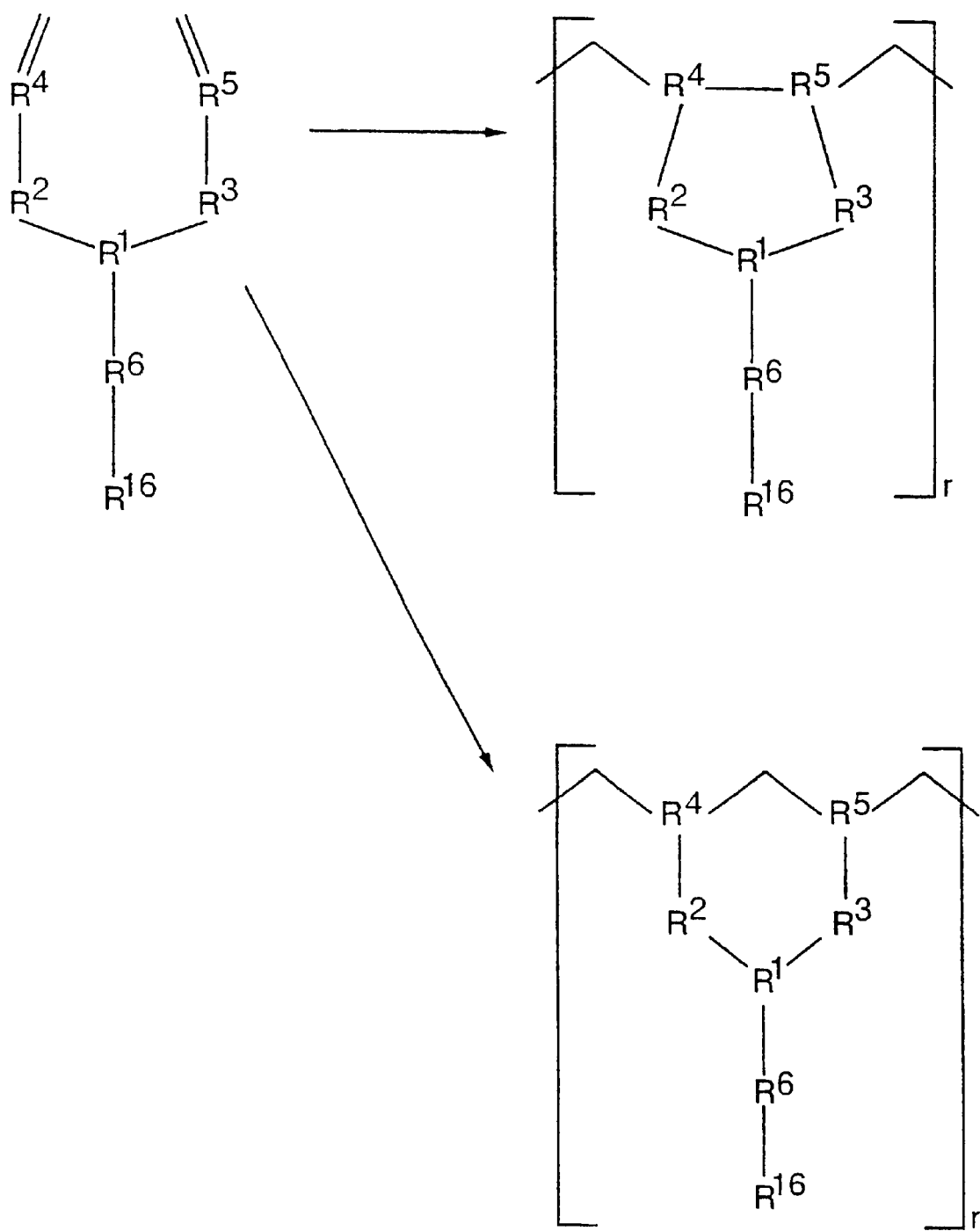

having two double bonds which are activated so that they will take part in a polymerization reaction, the double bonds being sufficiently close together to ensure that cyclopolymerization will preferentially occur. These compounds are used as monomers which preferentially are cyclopolymerized under the influence of ultraviolet or thermal radiation in the production of network polymers, for example coatings or binders.

29 Claims, 2 Drawing Sheets

POLYMERISATION

COPOLYMERISATION

DIALLYLAMINE MONOMERS AND NETWORK POLYMERS OBTAINED THEREFROM

The present invention relates to monomers which are useful in the production of polymers, and in particular to network polymers, to the polymers obtained therefrom and to methods of producing these polymers, in particular using radiation curing, for example ultraviolet or thermal radiation.

Many polymers such as polyethylenes, polystyrenes, polyvinylidene fluorides, polytetrafluoroethylenes (e.g. teflon™), nylons, polyesters etc. are used every day in a wide variety of purposes from plastic wrap and plastic cups to sensors and non-stick surfaces to yield high strength materials.

WO 98/29107 describes certain polydiallyamine-based bile acid sequestrants, which are formed by polymerisation of the monomer in solution.

The applicants have found that certain compounds with two or more multiple bonds may be activated by the presence of an electron withdrawing group, in particular where the electron withdrawing group is at a position which is alpha or beta to one or both of the double bonds to make them polymerisable, for example under the influence of radiation or an electron beam, or in the presence of a chemical initiator. Polymeric compounds obtained therefrom include cyclic rings. These have many advantageous properties. In particular, the invention can be used to generate products such as network polymers or conducting polymers depending upon the other aspects of the structure of the compounds.

Certain monomers are new and these form a further aspect of the invention. In particular, the invention provides a compound of formula (I)

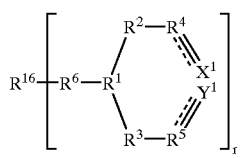
[I]

where $R^1$ is CH and $R^6$ is a bond, or $R^1$ and $R^6$ together form an electron withdrawing group;

$R^2$ and $R^3$ are independently selected from $(CR^7R^8)_n$, or a group $CR^9R^{10}$, $-(CR^7R^8CR^9R^{10})-$ or $-(CR^9R^{10}CR^7R^8)-$ where n is 0, 1, or 2, $R^7$ and $R^8$ are independently selected from hydrogen or alkyl, and either one of $R^9$ or $R^{10}$ is hydrogen and the other is an electron withdrawing group, or $R^9$ and $R^{10}$ together form an electron withdrawing group, and $R^4$ and $R^5$ are independently selected from CH or $CR^{11}$ where $R^{11}$ is an electron withdrawing group;

the dotted lines indicate the presence or absence of a bond, and $X^1$ is a group $CX^2X^3$ where the dotted line bond to which it is attached is absent and a group $CX^2$ where the dotted line bond to which it is attached is present, $Y^1$ is a group $CY^2Y^3$ where the dotted line bond to which it is attached is absent and a group $CY^2$ where the dotted line bond to which it is attached is present, and $X^2$, $X^3$, $Y^2$ and $Y^3$ are independently selected from hydrogen and fluorine;

$R^{16}$ is a bridging group of valency r and r is an integer of 2 or more, subject to the following provisos:
(i) that at least one of (a) $R^1$ and $R^6$ or (b) $R^2$ and $R^3$ or (c) $R^4$ and $R^5$ includes an electron withdrawing group.

Preferably the compounds of formula (I) are of formula (IA)

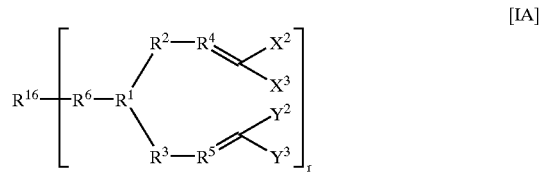

where $R^1$, $R^2$, $R^3$, $R^4$, $R^5$, $R^6$, $R^{16}$, $X^2$, $X^3$, $Y^2$ and $Y^3$ are as defined in relation to formula (I).

Suitably the compounds of formula (IA) are subject to the further proviso:
(ii) that where $R^{16}$ is a group $-(CH_2)_{10}-$, $R^2$ and $R^3$ are $CH_2$ groups, $R^4$ and $R^5$ are CH groups and $X^1$, $X^2$, $X^3$ and $X^4$ hydrogen, $R^1$ is other than a group $N^+CH_3Br^-$ where $R^6$ is a bond.

Suitably, where $R^{16}$ is a alkylene group, $R^2$ and $R^3$ are $CH_2$ groups, $R^4$ and $R^5$ are CH groups, $X^1$, $X^2$, $X^3$ and $X^4$ hydrogen, $R^1$ is other than a group $N^+R^{12}$ $(Z^{m-})_{1/m}$ as hereinafter defined, where $R^6$ is a bond.

Preferably, where $R^2$ and $R^3$ are both $(CR^7R^8)_n$, at least one n is 1 or 2. Suitably in formula (I), n is 1 or 2.

On polymerisation of these compounds, networks are formed whose properties may be selected depending upon the precise nature of the $R^{16}$ group, the amount of diluent, plasticiser or chain terminator present and the polymerisation conditions employed. Polymerisation will occur in accordance with the general scheme set out in FIG. 1 hereinafter.

When the dotted bonds in sub formula (I) are present, the resulting polymer will comprise polyacetylene chains. This can lead to a conjugated system and consequently a conducting polymer.

Suitably the compound is designed such that it cyclopolymerises under the influence of ultraviolet or thermal radiation, preferably. ultraviolet radiation. Cyclopolymerisation may take place either spontaneously in the presence of the appropriate radiation or in the presence of a suitable initiator, for example 2,2'-azobisisobutyronitrile (AIBN), aromatic ketones such as benzophenones in particular acetophenone; chlorinated acetophenones such as di- or tri-chloroacetophenone; dialkoxyacetophenones such as dimethoxyacetophenones (sold under the Trade name "Irgacure 651"); dialkylhydroxyacetophenones such as dimethylhydroxyacetophenone (sold under the Trade name "Darocure 1173"); substituted dialkylhydroxyacetophenone alkyl ethers such compounds of formula

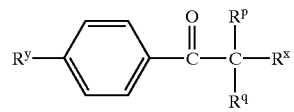

where $R^y$ is alkyl and in particular 2,2-dimethylethyl, $R^x$ is hydroxy or halogen such as chloro, and $R^p$ and $R^q$ independently selected from alkyl or halogen such as chloro (examples of which are sold under the Trade names "Darocure 1116" and "Trigonal P1"); 1-benzoylcyclohexanol-2 (sold under the Trade name "Irgacure 184"); benzoin or derivatives such as benzoin acetate, benzoin alkyl ethers in particular benzoin butyl ether, dialkoxybenzoins such as dimethoxybenzoin or deoxybenzoin; dibenzyl ketone; acyloxime esters such as methyl or ethyl esters of acyloxime (sold under the trade name "Quantaqure PDO"); acylphosphine oxides, acylphosphonates such as dialkylacylphosphonate, ketosulphides for example of formula

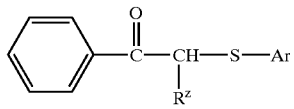

where $R^z$ is alkyl and Ar is an aryl group; dibenzoyl disulphides such as 4,4'-dialkylbenzoyldisulphide; diphenyldithiocarbonate; benzophenone; 4,4'-bis(N,N-dialkylamino)benzophenone; fluorenone; thioxanthone; benzil; or a compound of formula

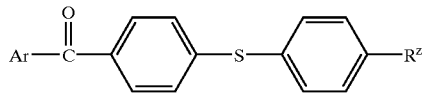

where Ar is an aryl group such as phenyl and $R^z$ is alkyl such as methyl (sold under the trade name "Speedcure BMDS"). The compound may be polymerised under the influence of a free radical or ion initiator as is understood in the art, as well as by application of an electron beam.

As used herein, the term "alkyl" refers to straight or branched chain alkyl groups, suitably containing up, to 20 and preferably up to 6 carbon atoms. The terms "alkenyl" and "alkynyl" refer to unsaturated straight of branched chains which include for example from 2–20 carbon atoms, for example from 2 to 6 carbon atoms. Chains may include one or more double or triple bonds respectively. In addition, the term "aryl" refers to aromatic groups such as phenyl or naphthyl.

The term "hydrocarbyl" refers to any structure comprising carbon and hydrogen atoms. For example, these may be alkyl, alkenyl, alkynyl, aryl such as phenyl or napthyl, aralkyl, cycloalkyl, cycloalkenyl or cycloalkynyl. Suitably they will contain up to 20 and preferably up to 10 carbon atoms. The term "heterocyclyl" includes aromatic or non-aromatic rings, for example containing from 4 to 20, suitably from 5 to 10 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

The term "functional group" refers to reactive groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(CO)_nR^6$, $-NR^aCONR^bR^c$, $-C=NOR^a$, $-N=CR^bR^c$, $S(O)_tNR^bR^c$, $C(S)_nR^a$, $C(S)OR^a$, $C(S)NR^bR^c$ or $-NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as $S(O)_s$, oxygen and nitrogen, n is an integer of 1 or 2, t is 0 or an integer of 1–3. In particular the functional groups are groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $-NR^aCSNR^bR^c$, $-C=NOR^a$, $-N=CR^bR^c$, $S(O)_tNR^bR^c$, or $-NR^bS(O)_tR^a$ where $R^a$, $R^b$ and $R^c$, n and t are as defined above.

The term "heteroatom" as used herein refers to non-carbon atoms such as oxygen, nitrogen or sulphur atoms.

Where the nitrogen atoms are present, they will generally be present as part of an amino residue so that they will be substituted for example by hydrogen or alkyl.

The term "amide" is generally understood to refer to a group of formula $C(O)NR^aR^b$ where $R^a$ and $R^b$ are hydrogen or an optionally substituted hydrocarbyl group. The term "sulphonamide" correspondingly relates to groups of formula $S(O)_2NR^aR^b$.

The nature of the electron withdrawing group or groups used in any particular compound of formula (I) will depend upon its position in relation to the double bond it is required to activate, as well as the nature of any other functional groups within the compound.

In a preferred embodiment, $R^1$ and $R^6$ form an electron withdrawing group. For example, $R^1$ is a heteroatom or a substituted heteroatom which has electron withdrawing properties, for example a group $N^+R^{12}(Z^{m-})_{1/m}$, $S(O)_pR^{13}$, B, $P(O)_qR^{14}$ or $Si(R^{15})$ where $R^{12}$, $R^{13}$, $R^{14}$ and $R^{15}$ are independently selected from hydrogen or hydrocarbyl, Z is a anion of valency m, p is 0, 1 or 2, and q is 0, 1, 2 or 3; and $R^6$ is a bond. Alternatively, $R^1$ is a group CH and $R^6$ is a group $-C(O)O-$, $-OC(O)-$ or $S(O)_2$, suitably $C(O)O-$, or $-OC(O)-$ and preferably $S(O)_2$. In yet a further alternative, $R^1$ and $R^6$ form an amide or sulphonamide group where $R^1$ is nitrogen and $R^6$ is $C(O)$ or $S(O)_2$.

Most preferably, $R^1$ is a group $N^+R^{12}(Z^{m-})_{1/m}$, $S(O)_pR^{13}$, B, $P(O)_qR^{14}$ or $Si(R^{15})$ where $R^{12}$, $R^{13}$, $R^{14}$ and $R^{15}$ are independently selected from hydrogen or alkyl in particular $C_{1-3}$ alkyl, Z is a halogen. In particular $R^1$ is a group $N^+R^{12}(Z^{m-})_{1/m}$, and $R^6$ is a bond. The nature of the anion Z will affect the physical properties of the final polymer such as its porosity, water retention and in particular, its conductivity. Suitable anions for the Z group include halide ions such as fluoride, chloride, bromide or iodide, borides such as boron tetrafluoride; carboxylic acid esters such as those of formula $R^{14}C(O)O^-$ where $R^{14}$ is an optionally substituted hydrocarbyl group group such as haloalkyl, in particular trifluoromethyl; and other anionic groups such as mesylate and tosylate. In general, the water permeability of the ultimate polymer will vary as follows:

Other factors which affect the water permeability of the polymer is the nature of the bridging group. When this contains for example perhaloalkyl substituents such as perfluoroalkyl, it will be largely water impermeable as compared to polymers which have alkylene bridging groups optionally interposed with say oxygen.

In a particular embodiment, the combination of $R^1$ and $R^6$ forms an amide group or sulphonamide group, where $R^1$ is a nitrogen atom and $R^6$ is a carbonyl group or sulphonyl group.

Alternatively, where the activation is effected by electron withdrawing groups at a position indicated by $R^2$ or $R^3$, suitable electron withdrawing groups $R^9$ and $R^{10}$ include $COCH_2CN$ and $COCH_3$ preferably $R^9$ and $R^{10}$ together form an oxo group.

Where $R^{11}$ is an electron withdrawing group, it is suitably $COCH_3$. Preferably, $X^2$, $X^3$, $Y^2$ and $Y^3$ are all hydrogen.

Suitably r is an integer of from 2 to 6, preferably from 2 to 4. The polymers produced can be useful in a number of different applications including the production of network polymers and those used in thermal management.

Thermal management is the control of optical properties of materials across solar and thermal wavebands (~0.7–12 microns). This control of transmitted, reflected and absorbed radiation gives the potential to design systems that can selectively perform different tasks at different wavelengths. For example use of silver coatings by the glazing industry to limit solar transmission (material transparent at visible wavelengths but reflective across the solar) and thus prevent 'greenhouse' heating. Other example could be solar water heaters where the material is transparent at NIR wavelengths but reflective at longer wavelengths. Benefits of thermal management could be in reduced air conditioning/heating costs.

The properties of the polymer obtained in accordance with the invention will depend upon a variety of factors but will depend very largely on the nature of the group $R^{16}$.

Suitably $R^{16}$ will comprise a bridging group for example as is known in polymer, paint or coating chemistry. These may include straight or branched chain alkyl groups, optionally substituted or interposed with functional groups or siloxane groups such as alkyl siloxanes. Suitable bridging groups include those found in polyethylenes, polypropylenes, nylons, as listed in Table 1.

TABLE 1

| Polymer type | Repeat Unit of Bridging Group |
|---|---|
| Polyethylene | $CH_2$ |
| Polystyrene | $CH_2CH(C_6H_5)$ where the phenyl ring is optionally substituted |
| Polyisobutylene | $CH_2CH(CH(CH_3)_2)$ |
| Polyisoprene | $CH_2CH(CH_3)$ |
| Polytetrafluoroethylene | $CH_2(CF_2)_xCH_2$ |
| Polyvinylidenefluoride | $CH_2(CF_2H_2)_x$ |
| polyethyleneoxide | $(OCH_2CH(CH_3))_xO$ |
| Nylon | $CH_2(NHCOCH_2)_xCH_2$ |
| Peptide | $CH_2(NHCOCH_R)_xCH_2$ |
| Polyurethanes | —NH—CO—O— |
| Polyesters | —RC(O)OR'— where R and R' are organic groups such as hydrocarbyl |
| Polysiloxanes | e.g. —$SiO_2$—, —$R_2SiO$— or —$R_2Si_2O_3$— where R is an organic group such as hydrocarbyl |
| Polyacrylates | —$CH_2C(COOH)H$— |
| Polyureas | —NHCONH— |
| Polythioureas | —NH—C(S)—NH— |

The length of the bridging group will affect the properties of the polymeric material derived from this. This can be used to design polymers with properties which are best suited to the application. For instance when the bridging group comprises relatively long chains, (for example with in excess of 6 repeat units, for example from 6–20 repeat units), the polymer will have pliable plastic properties. Alternatively, when the bridging group is relatively short, (e.g. less than 6 repeat units) the material will be more brittle.

Other possibility for producing particular properties arises from the possibility of producing copolymers where another monomeric compound, for example one which is not of formula (I), is mixed with the compound of formula (I) prior to polymerisation. Such monomers are known in the art. They include diallyamine compounds as well as others conventionally used.

Composites may also be produced by polymerising compounds of formula (I) in the presence of other moieties such as graphite, ethers such as crown ethers or thioethers, thalocyanines, bipyridyls or liquid crystal compounds, all of which will produce composite polymers with modified properties.

Examples of possible bridging groups $R^{16}$ where r is 2 are groups of sub-formula (II)

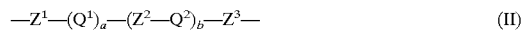

where a and b are independently selected from 0, 1 or 2, $Z^1$, $Z^2$ and $Z^3$ are independently selected from a bond, an optionally substituted linear or branched alkyl or alkene chain wherein optionally one or more non-adjacent carbon atoms is replaced with a heteroatom or an amide group, $Q^1$ and $Q^2$ are independently selected from an optionally substituted carbocyclic or heterocyclic ring which optionally contains bridging alkyl groups;

a and b are independently selected from 0, 1 or 2.

Suitable carbocyclic rings for $Q^1$ and $Q^2$ include cycloalkyl groups for example of from 1 to 20 carbon atoms. Bridged carbocyclic ring structures include 1,4-bicyclo [2.2.2]octane, decalin, bicyclo[2.2.1]heptane, cubane, diadamantane, adamantane. Suitable heterocyclic rings include any of the above where one or more non adjacent carbon atoms are replaced by a heteroatom such as oxygen, sulphur or nitrogen (including amino or substituted amino), or a caboxyl or an amide group. Suitable optional substitutents for the groups $Q^1$ and $Q^2$ include one or more groups selected from alkyl, alkenyl, alkynyl, aryl, aralkyl such as benzyl, or functional groups as defined above. Particularly substitutents for the groups $Q^1$ and $Q^2$ are oxo and halogen in particular fluorine and chlorine.

Suitable optional substituents for the alkyl and alkene groups $Z^1$, $Z^2$ and $Z^3$ include aryl, aralkyl and functional groups as defined above. Particular substituents include halogens such as fluorine and chlorine, and oxo.

Other sorts of bridging groups $R^{16}$ include electrically conducting chains, for instance, electrically conducting unsaturated chains such as alkenes or chains incorporating aromatic or heterocyclic rings. For instance, the group $R^{16}$ in a compound of formula (I) may comprise a di substituted conducting unit such as a tertathiafulvalene. Thus an example of a compound of formula (I) is a compound of formula (III

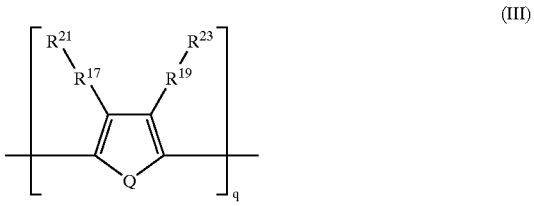

where $R^{21}$ and $R^{23}$ are each groups of sub-formula (IV)

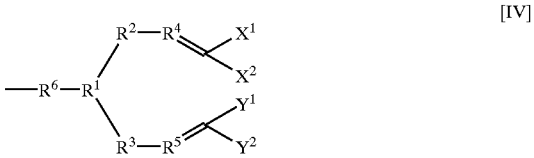

where $X^2$, $X^3$, $Y^2$, $Y^3$, $R^1$, $R^2$, $R^3$, $R^4$, $R^5$ and $R^6$ are as defined in relation to formula (I) above and $R^1$ and $R^{19}$ are independently selected from groups of sub-formula (II) as given above, q is an integer of 1 or more, for example from 1 to 6, and Q is sulphur or NH. In particular $R^{17}$, $R^{18}$, $R^{19}$ and $R^{20}$ are alkyl groups.

Polymerisation of compounds of formula (III) will give cross-linked networks where the cross-linking occurs through the diene units. This will lead to a very stable material with robust physical properties. Once again, varying the length of the spacer groups $R^{17}$, $R^{18}$, $R^{19}$ and $R^{20}$ will lead to materials with designer properties. For instance when $R^{17}$, $R^{18}$, $R^{19}$ and $R^{20}$ are relatively long chains, the polymer will have pliable plastic properties. Alternatively, when the chains $R^{17}$, $R^{18}$, $R^{19}$ and $R^{20}$ are relatively short, the material will be more brittle.

Where $R^1$ and $R^6$ together form a group —$N^+R^7Z^-$, varying the counter ion $Z^-$ can also be used to adjust the physical properties of the polymer, such as water retention, porosity or conductivity. The materials will exhibit conducting properties, making them suitable as organic semiconductors for example for use as interconnects for IC chips etc.

Alternatively, a bridging group $R^{16}$ may comprise a tetra or octa substituted non-linear optic unit such as an optionally substituted porphyrin or phthalocyanine. Suitable optional substitutents in addition to the groups of sub-formula (I) are hydrocarbyl groups such as alkyl in particular methyl. An example of such a compound is a compound of formula (VI)

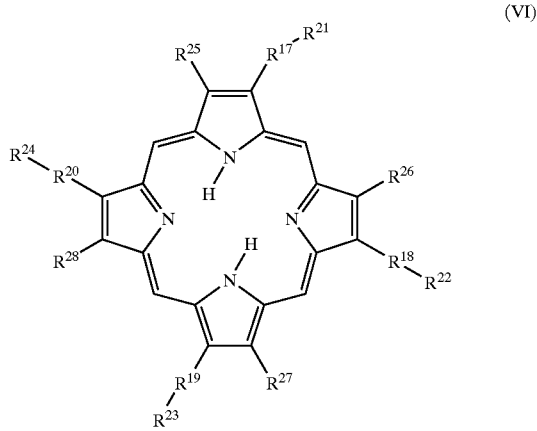

(VI)

where $R^{17}$, $R^{18}$, $R^{19}$, $R^{20}$, $R^{21}$, $R^{22}$, $R^{23}$ and $R^{24}$ are as defined in relation to formula (III) above and $R^{25}$, $R^{26}$, $R^{27}$ and $R^{28}$ are each independently selected from hydrogen or hydrocarbyl groups such as alkyl and in particular methyl; and the compound optionally contains a metal ion within the macrocyclic heterocyclic unit. An alternative compound is a compound of formula (VIA)

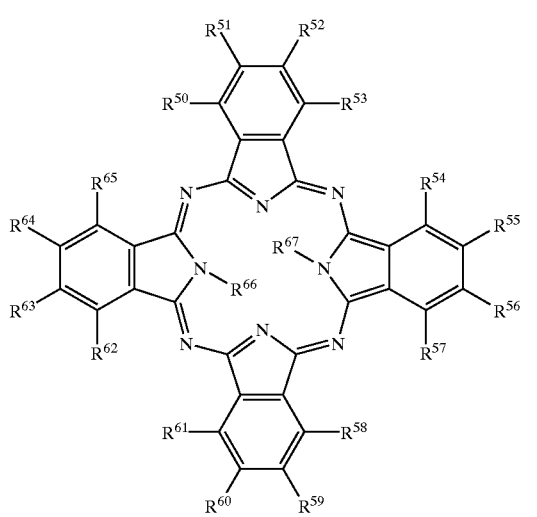

(VIA)

where $R^{50}$ through to $R^{65}$ are independently selected from hydrocarbyl in particular $C_{1-12}$ alkyl, a group $OR^{68}$ where $R^{68}$ is hydrocarbyl in particular butyl, halogen in particular chlorine or a group $R^{24}$–$R^{28}$ where $R^{24}$ and $R^{28}$ are as defined in relation to formula (III) above, provided that at least two of $R^{50}$ to $R^{65}$ are $R^{24}$–$R^{28}$ groups, and $R^{66}$ and $R^{67}$ are either hydrogen or together comprise a metal ion such as a copper ion.

Preferably in formula (VIA), $R^{51}$, $R^{52}$, $R^{55}$, $R^{56}$, $R^{59}$, $R^{60}$, $R^{63}$ and $R^{64}$ are halogen and $R^{50}$, $R^{53}$, $R^{54}$, $R^{57}$, $R^{58}$, $R^{61}$, $R^{62}$ and $R^{65}$ are independently $C_{1-12}$ alkyl, $C_{1-12}$ alkoxy or a group $R^{24}$–$R^{28}$.

Polymerisation of a compound of formula (VI) or (VIA) in accordance with the scheme of FIG. 1, for example by photopolymerisation will provide a cross linked network polymer where the cross linking occurs through the diene units for example as either quaternery ammonium salts or amides depending upon the particular nature of the groups $R^1$ and $R^6$ present in the $R^{21}$, $R^{22}$, $R^{23}$ and $R^{24}$ units. Again this can produce a very stable network or elastomeric material with robust physical properties. In addition to conductivity, these polymers will be capable of exhibiting third order polarisabilities and they will be suitable for applications which employ the Kerr effect. These properties can be affected or moderated when metals or metal ions are inserted into the macrocyclic heterocyclic unit. Suitable metal ions include sodium, potassium, lithium, copper, zinc and iron ions.

Yet a further possibility for the bridging group $R^{16}$ is a polysiloxane network polymer where $R^{16}$ comprises a straight or branched siloxane chain of valency r or a cyclic polysiloxane unit.

Thus compounds of structure (VII)

(VII)

$$R^{21}-R^{17}-\underset{R^{29}}{\overset{R^{28}}{Si}}-O-[\underset{R^{33}}{\overset{R^{32}}{Si}}-O]_u-\underset{R^{31}}{\overset{R^{30}}{Si}}-R^{18}-R^{22}$$

where $R^{17}$, $R^{18}$, $R^{21}$ and $R^{22}$ are as defined above in relation to formula (III), $R^{28}$, $R^{29}$, $R^{30}$ are $R^{31}$, are selected from hydrocarbyl such as alkyl and in particular methyl, and each $R^{32}$ or $R^{32}$ group is independently selected from hydrocarbyl or a group of formula $R^{19}$–$R^{23}$ where $R^{19}$ and $R^{23}$ are as defined above in relation to formula (III), and u is 0 or an integer of 1 or more, for example of from 1 to 20; and (VIII)

(VIII)

where $R^{17}$, $R^{18}$, $R^{19}$, $R^{20}$, $R^{21}$, $R^{22}$, $R^{23}$ and $R^{24}$ are as defined above in relation to formula (III) and $R^{28}$, $R^{29}$, $R^{30}$ and $R^{31}$ are as defined above in relation to formula (VII), and r is 0 or an integer of 1 or more, for example from 1 to 5. In a particular embodiment, formula (VIII) has four siloxane units in the ring (i.e. r is 1). It will be appreciated that there may be other numbers of such units in the, cyclic ring, for example from 3 to 8 siloxane units (r is from 0 to 5), preferably from 3 to 6 siloxane units(r is from 0 to 3).

In the above structures (VII) and (VIII), it will be appreciated that —Si— may be replaced by B or B⁻; or —Si—O— is replaced by —B—N($R^{40}$)— where $R^{40}$ is a hydrocarbyl group such as those defined above in relation to group $R^{32}$ in formula (VII) or a group —$R^{24}$–$R^{28}$ as defined in relation to formula (VIII) above.

Upon polymerisation, compounds of formula (VII) and (VIII) or variants thereof, will form a cross-linked network where the cross-linking occurs through the groups $R^{21}$, $R^{22}$, $R^{23}$ and $R^{24}$ as illustrated in FIG. 1. Such polymers may exhibit properties similar to those of conventional siloxanes. However, in the case of compounds of formula (VII) and (VIII), they may be coated onto surfaces and polymerised in situ, for example using radiation curing.

Further examples of compounds of formula (I) include compounds of formula (IX)

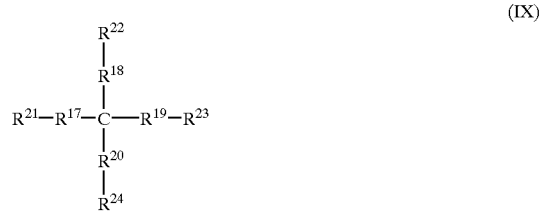

(IX)

where $R^{17}$, $R^{18}$, $R^{19}$, $R^{20}$, $R^{21}$, $R^{22}$, $R^{23}$ and $R^{24}$ are as defined above in relation to formula (III).

Particular examples of compounds of formula (I) and related compounds are listed in Table 2 below:

TABLE 2

$$R^{16}\!-\!\!\left[R^6\!-\!R^1\genfrac{}{}{0pt}{}{\overset{R^2-R^4}{\diagup\;\;\;\diagdown}}{\underset{R^3-R^5}{\diagdown\;\;\;\diagup}}\right]_r$$

| No. | $R^{16}$ | $R^6$ | $R^1$ | $R^2$ | $R^3$ | $R^4$ | $R^5$ | r |
|---|---|---|---|---|---|---|---|---|
| 1 | —(CH₂)₁₀— | bond | N⁺HCF₃COO⁻ | CH₂ | CH₂ | CH | CH | 2 |
| 2 | (CH₂)₁₀— | bond | N⁺H(PF₆)⁻ | CH₂ | CH₂ | H | CH | 2 |
| 3 | (CH₂)₁₀— | bond | N⁺HCl⁻ | CH₂ | CH₂ | CH | CH | 2 |
| 4 | (CH₂)₁₀— | bond | N⁺CH₃I⁻ | CH₂ | CH₂ | CH | CH | 2 |
| 5 | —CH₂(OCH₂CH₂)₂OCH₂— | OC(O) | CH | — | — | CH | CH | 2 |
| 6 | CH₂—(OCH₂CH₂)₂OCH₂ | OC(O) | CH | — | CH₂ | CH | CH | 2 |
| 7 | CH₂—(OCH₂CH₂)₂OCH₂ | C(O) | N | CH₂ | CH₂ | CH | CH | 2 |
| 8 | CH₂—(OCH₂CH₂)₂OCH₂ | OC(O) | CCH₃ | CH₂ | CH₂ | CH | CH | 2 |
| 9 | CH₂O(CH₂)₅OCH₂ | OC(O) | CH | — | CH₂ | CH | CH | 2 |
| 10 | CH₂(OCH₂CH₂)₁₂OCH₂ | C(O) | N | CH₂ | CH₂ | CH | CH | 2 |
| 11 | (CH₂)₈ | C(O) | N | CH₂ | CH₂ | CH | CH | 2 |
| 12 | (CH₂)₁₈ | C(O) | N | CH₂ | CH₂ | CH | CH | 2 |
| 13 | CH₂CH₂ | bond | N⁺H(PF₆)⁻ | CH₂ | CH₂ | CH | CH | 2 |
| 14 | (CF₂)₁₀ | CO | N | CH₂ | CH₂ | CH | CH | 2 |
| 15 | (CH₂)₈ | OC(O) | CH | — | — | CH | CH | 2 |
| 16 | (CH₂)₁₂ | bond | N⁺CH₃I⁻ | CH₂ | CH₂ | CH | CH | 2 |
| 17 | CH₂OCH₂CH₂OCH₂ | C(O) | N | CH₂ | CH₂ | CH | CH | 2 |
| 18 | >CH—CH< | C(O) | N | CH₂ | CH₂ | CH | CH | 4 |
| 19 | CH₂(OCH₂CH₂)₁₂OCH₂ | OC(O) | CH | — | — | CH | CH | 2 |
| 20 | —(CH₂)₁₀— | bond | N⁺H(BF₄)⁻ | CH₂ | CH₂ | CH | CH | 2 |
| 21 | —(CH₂)₈— | OC(O) | CH | — | CH₂ | CH | CH | 2 |
| 22 | —(CH₂)₈— | OC(O) | CH | CH₂ | CH₂ | CH | CH | 2 |
| 23 | —(CH₂)₈— | OC(O) | CH | CH\|Me | CH\|Me | CH | CH | 2 |
| 24 | —(CH₂)₈— | OC(O) | CH | — | CH₂ | C\|Me | C\|Me | 2 |
| 25 | —(CH₂)₈— | OC(O) | CH | CH₂ | CH₂ | C\|Me | C\|Me | 2 |
| 26 | CH₂O(CH₂)OCH₂ | OC(O) | CH | — | CH₂ | CH | CH | 2 |
| 27 | CH₂—(OCH₂CH₂)₂OCH₂ | OC(O) | CCH₃ | CH₂ | CH₂ | CH | CH | 2 |
| 28 | CH₂CH₂ | bond | N⁺H(Cl)⁻ | CH₂ | CH₂ | CH | CH | 2 |
| 29 | CH₂CH₂CH₂ | bond | N⁺H(Cl)⁻ | CH₂ | CH₂ | CH | CH | 2 |
| 30 | (CH₂)₆ | bond | N⁺H(Cl)⁻ | CH₂ | CH₂ | CH | CH | 2 |
| 31 | (CH₂)₉ | bond | N⁺H(Cl)⁻ | CH₂ | CH₂ | CH | CH | 2 |
| 32 | (CH₂)₆ | bond | N⁺CH₃(I)⁻ | CH₂ | CH₂ | CH | CH | 2 |
| 33 | (CH₂)₁₂ | bond | N⁺H(Cl)⁻ | CH₂ | CH₂ | CH | CH | 2 |
| 34 | (CH₂)₁₀ | bond | N⁺H((SO₄)/2)⁻ | CH₂ | CH₂ | CH | CH | 2 |
| 35 | (CF₂)₈ | CO | N | CH₂ | CH₂ | CH | CH | 2 |
| 36 | —(CH₂)₃C(O)NH(CH₂)₂NHC(O)(CH₂)₃— | CO | N | CH₂ | CH₂ | CH | CH | 2 |

TABLE 2-continued $$R^{16}\!-\![R^6\!-\!R^1\underset{R^3\!-\!R^5}{\overset{R^2\!-\!R^4}{\diagdown}}]_r$$

| No. | R[16] | R[6] | R[1] | R[2] | R[3] | R[4] | R[5] | r |
|---|---|---|---|---|---|---|---|---|
| 37 | —(CH$_2$)$_3$C(O)NH(CH$_2$)$_6$NHC(O)(CH$_2$)$_3$— | CO | N | CH$_2$ | CH$_2$ | CH | CH | 2 |
| 38 | —(CH$_2$)$_3$C(O)NH(CH$_2$)$_{12}$NHC(O)(CH$_2$)$_3$— | CO | N | CH$_2$ | CH$_2$ | CH | CH | 2 |
| 39 | —(CH$_2$)$_3$C(O)O(CH$_2$)$_3$OC(O)(CH$_2$)— | CO | N | CH$_2$ | CH$_2$ | CH | CH | 2 |
| 40 | —(CH$_2$)$_3$C(O)O(CH$_2$)$_{10}$OC(O)(CH$_2$)— | CO | N | CH$_2$ | CH$_2$ | CH | CH | 2 |
| 41 | —(CH$_2$)$_2$COO—C$_6$H$_4$—C$_6$H$_4$—OCO(CH$_2$)$_2$— | CO | N | CH$_2$ | CH$_2$ | CH | CH | 2 |
| 42 | —(CH$_2$)$_3$C(O)(OCH$_2$CH$_2$)$_3$OC(O)—(CH$_2$)$_2$— | CO | N | CH$_2$ | CH$_2$ | CH | CH | 2 |
| 43 | —(CH$_2$)$_3$C(O)NH[(CH$_2$)$_3$OCH$_2$CH$_2$)$_3$CH$_2$]NHC(O)(CH$_2$)$_3$— | CO | N | CH$_2$ | CH$_2$ | CH | CH | 2 |
| 44 | —(CH$_2$)$_2$C(O)OCH$_2$(CF$_2$)$_6$CH$_2$OC(O)(CH$_2$)$_2$— | CO | N | CH$_2$ | CH$_2$ | CH | CH | 2 |
| 45 | —(CH$_2$)$_3$C(O)OCH$_2$(CF$_2$)$_6$CH$_2$OC(O)(CH$_2$)$_3$— | CO | N | CH$_2$ | CH$_2$ | CH | CH | 2 |
| 46 | —(CF$_2$)$_3$C(O)OCH$_2$(CF$_2$)$_6$CH$_2$OC(O)(CF$_2$)$_3$— | CO | N | CH$_2$ | CH$_2$ | CH | CH | 2 |
| 47 | —(CF$_2$)$_3$C(O)OC(O)(CF$_2$)$_3$— | CO | N | CH$_2$ | CH$_2$ | CH | CH | 2 |
| 48 | —(CH$_2$)$_3$C(O)NH(CH$_2$)$_3$Si(CH$_3$)$_2$OSi(CH$_3$)$_2$(CH$_2$)$_3$NHC(O)(CH$_2$)$_3$— | CO | N | CH$_2$ | CH$_2$ | CH | CH | 2 |
| 49 | —(CH$_2$)$_3$CONH—(C$_6$H$_{10}$)—CH$_2$—(C$_6$H$_{10}$)—NHCO(CH$_2$)$_3$— | CO | N | CH$_2$ | CH$_2$ | CH | CH | 2 |
| 50 | —(CH$_2$)$_3$COO—(tetrathia-macrocycle)—OCO(CH$_2$)$_3$— | CO | N | CH$_2$ | CH$_2$ | CH | CH | 2 |
| 51 | —(CH$_2$)$_2$C(O)O$^-$ $^+$NH$_3$(CH$_2$)$_3$(OCH$_2$CH$_2$)$_2$O(CH$_2$)$_3$N$^+$H$_3$ $^-$OC(O)(CH$_2$)$_2$— | CO | N | CH$_2$ | CH$_2$ | CH | CH | 2 |
| 52 | —CH$_2$CHCHCH$_2$— | CO | N | CH$_2$ | CH$_2$ | CH | CH | 4 |
| 53 | C[OC(O)(CH$_2$)$_3$—]$_4$ | CO | N | CH$_2$ | CH$_2$ | CH | CH | 4 |
| 54 | N[(CH$_2$)$_2$NHC(O)(CH$_2$)$_3$—]$_3$ | CO | N | CH$_2$ | CH$_2$ | CH | CH | 3 |
| 55 | N[(CH$_2$)$_2$OC(O)(CH$_2$)$_3$—]$_3$ | CO | N | CH$_2$ | CH$_2$ | CH | CH | 3 |
| 56 | 1,3,5-tris(butanoyloxy)benzene | CO | N | CH$_2$ | CH$_2$ | CH | CH | 3 |
| 57 | —CH$_2$C(OH)CH$_2$— with C(O)— branch | CO | N | CH$_2$ | CH$_2$ | CH | CH | 3 |
| 58 | —C(=CH$_2$)CH$_2$C(O)O—(CH$_2$)OC(O)CH$_2$C(=CH$_2$)— | CO | N | CH$_2$ | CH$_2$ | CH | CH | 2 |
| 59 | —CH=CHC(O)O(CH$_2$)$_{10}$OC(O)CH=CH— | CO | N | CH$_2$ | CH$_2$ | CH | CH | 2 |
| 60 | —NH(CH$_2$)$_6$NH— | CO | N | CH$_2$ | CH$_2$ | CH | CH | 2 |
| 61 | —NH(CH$_2$)$_{12}$NH— | CO | N | CH$_2$ | CH$_2$ | CH | CH | 2 |
| 62 | —(CH$_2$)$_3$OC(O)NH(CH$_2$)$_6$—NHC(O)O(CH$_2$)— | CO | N | CH$_2$ | CH$_2$ | CH | CH | 2 |
| 63 | —(CH$_2$)$_3$C(O)NH(CH$_2$)$_6$—NHC(O)(CH$_2$)— | CO | N | CH$_2$ | CH$_2$ | CH | CH | 2 | where — indicates a bond and Me is an abbreviation for methyl.

Compounds of formula (I) are suitably prepared by conventional methods, for example by reacting a compound of formula (X)

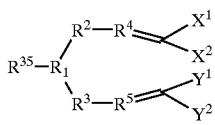 (X)

where $X^2$, $X^3$, $Y^2$, $Y^3$, $R^2$, $R^3$, $R^4$ and $R^5$ are as defined in relation to formula (I), $R^{1'}$ is a group $R^1$ as defined in relation to formula (I) or a precursor thereof, $R^{35}$ is hydrogen or hydroxy, with a compound of formula (XI)

$$R^{16}\text{---}[R^6\text{---}Z^4]_r \qquad (XI)$$

where $R^6$, $R^{16}$ and r are as defined in relation to formula (I) and $Z^4$ is a leaving group, and thereafter if desired or necessary converting a precursor group $R^{1'}$ to a group $R^1$.

Suitable leaving groups $Z^4$ include halogen, in particular bromo, mesylate or tosylate. The reaction is suitably effected in an organic solvent such as tetrahydrofuran, dichloromethane, toluene, an alcohol such as methanol or ethanol, or a ketone such as butanone and at elevated temperatures for example near the boiling point of the solvent.

Preferably the reaction is effected in the presence of a base such as potassium carbonate.

When the group $R^{1'}$ is a precursor of the group $R^1$, it may be converted to the corresponding $R^1$ group using conventional techniques. For example $R^{1'}$ may be a nitrogen atom, which may be converted to a group $NR^{12}(Z^{m-})_{1/m}$ where $R^{12}$, Z and m are as defined above, by reaction with an appropriate salt under conventional conditions. Examples of this are illustrated hereinafter.

Compounds of formulae (X) and (XI) are either known compounds or they can be prepared from known compounds by conventional methods.

Thus the invention further provides a method for producing a polymeric material, said method comprising causing a compound of formula (I) to polymerise. Suitably the compound of formula (I) is a radiation curable compound and polymerisation is effected by subjecting the compound to the appropriate radiation (e.g. heat or ultraviolet radiation) and if necessary in the presence of a suitable initiator such as a photoinitiator like AIBN. Where the compound of formula (I) cannot or it is not appropriate for it to be cured in this way, other conventional polymerisation techniques can be employed as would be understood in the art.

Radiation curing of compounds of formula (I) and related compounds form a further aspect of the invention. Thus the invention further provides a method of producing a polymer which comprises subjecting a compound of formula (IB)

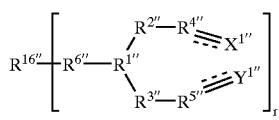 [IB]

where $R^{1''}$ is CH and $R^{6''}$ a bond, or $R^{1''}$ and $R^{6''}$ together form an electron withdrawing group;

$R^{2''}$ and $R^{3''}$ are independently selected from $(CR^{7''}R^{8''})_{n''}$, or a group $CR^{9''}R^{10''}$, —$(CR^{7''}R^{8''}CR^{9''}R^{10''})$— or —$(CR^{9''}R^{10''}CR^{7''}R^{8''})$— where n" is 0, 1 or 2, $R^{7''}$ and $R^{8''}$ are independently selected from hydrogen or alkyl, and either one of $R^{9''}$ or $R^{10''}$ is hydrogen and the other is an electron withdrawing group, or $R^{9''}$ and $R^{10''}$ together form an electron withdrawing group, and $R^{4''}$ and $R^{5''}$ are independently selected from CH or $CR^{11''}$ where $R^{11''}$ is an electron withdrawing group;

$X^{1''}$ and $Y^{1''}$ are groups as defined for $X^1$ and $Y^1$ respectively in relation to formula (I;

$R^{16''}$ is a bridging group of valency r" and r" is an integer of 2 or more, provided that at least one of (a) $R^{1''}$ and $R^{6''}$ or (b) $R^{2''}$ and $R^{3''}$ or (c) $R^{4''}$ and $R^{5''}$ includes an electron withdrawing group, to radiation under conditions which would cause the compound of formula (Ib) to polymerise.

Preferred groups in the compounds of formula (Ib) are those described above in relation to the corresponding groups of the compound of formula (I).

During the polymerisation process, the compounds of formula (I) (IA) or (IB) link together by way of the unsaturated bonds such as the diene groups as illustrated in FIG. 1. Because the compounds of formula (I), (IA) and (IB) include at least two diene groups, they will tend to become cross linked to form a network or three dimensional structure. The degree of cross linking can be controlled by carrying out the polymerisation in the presence of cross-linkers, where for example r is greater than 2, for example 4, or diluents, plasticisers or chain terminators. These will suitably comprise a compound of formula (XII)

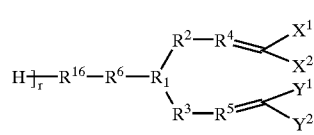 (XII)

where $X^1$, $X^2$, $Y^1$, $Y^2$, $R^1$, $R^2$, $R^3$, $R^4$, $R^5$, $R^6$, $R^{16}$ and r are as defined in relation to formula (I). Compounds of formula (I) may be used in the preparation of homopolymers or copolymers where they are mixed with other monomeric units, which may themselves be of formula (I) or otherwise.

Figure 2:
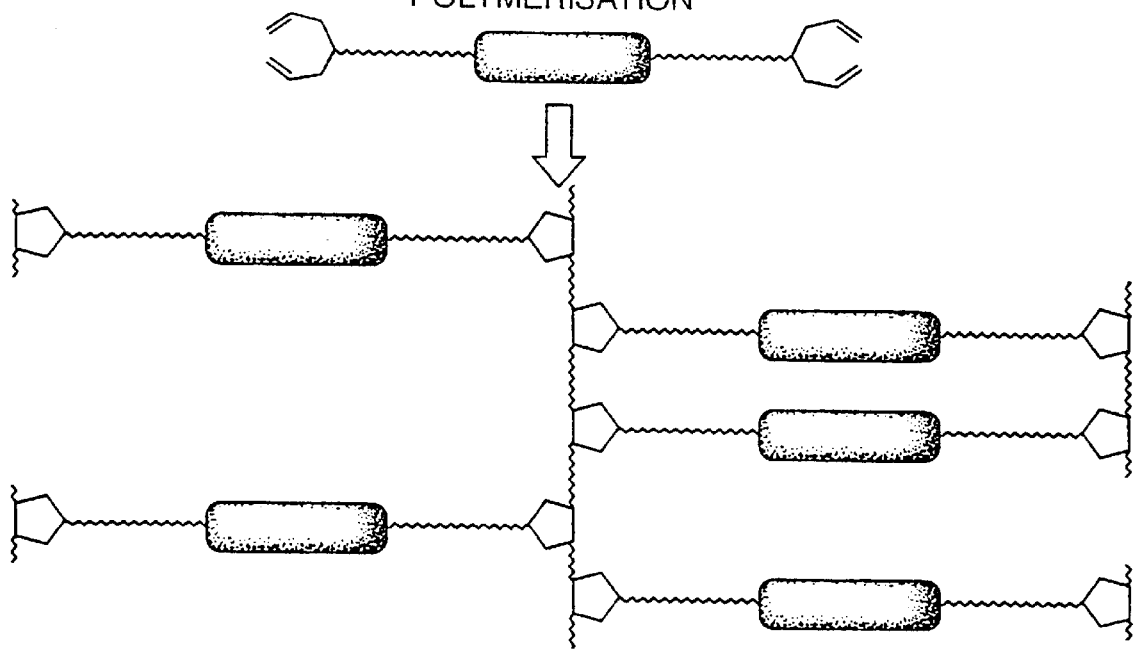
Figure 2:
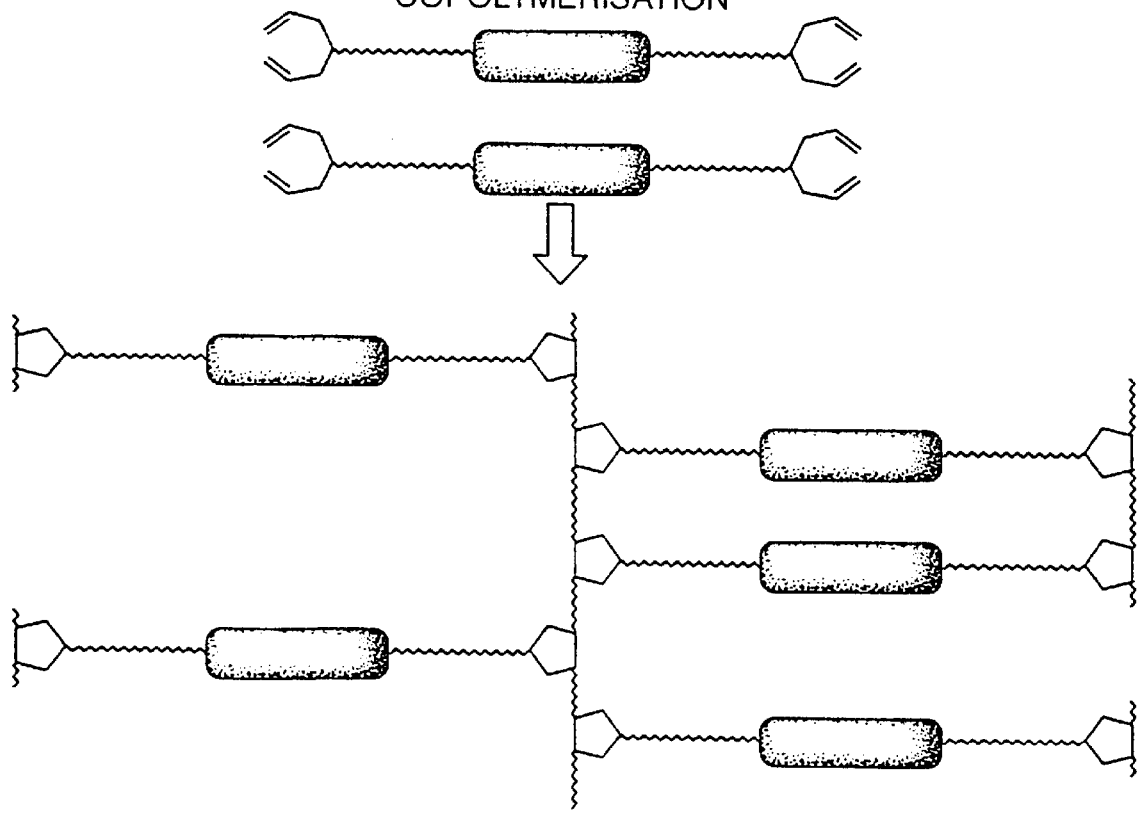

A general scheme illustrating the sort of polymerisation process which may occur using a polyethylene type bridging group is illustrated in FIG. 2.

Polymeric compounds obtained form a further aspect of the invention. Thus the invention further provides a polymeric compound of formula (XIII)

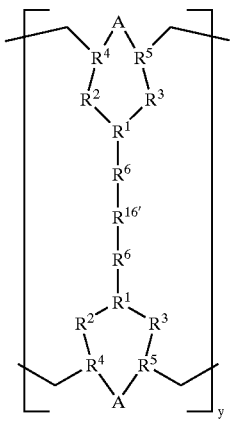

(XIII)

where A is a bond or or $CH_2$, $R^1$, $R^2$, $R^3$, $R^4$, $R^5$, $R^6$ are as defined in relation to formula (I), $R^{16'}$ is a group of formula $R^{16}$ as defined in formula (I) which may be substituted by further groups of sub formula (XIV)

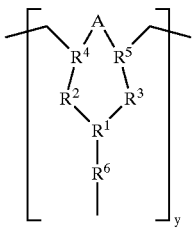

(XIV)

and y is an integer in excess of 1, preferably in excess of 5 and suitably from 5 to 30 and A is as defined above. It will be understood that copolymers also fall within the scope of this definition as outlined above.

Using the compounds of the invention, it is possible to take a suitable organic system that has optimal or optimised properties for use in certain applications, eg, high yield strength, large hyperpolarisability, high pyroelectric coefficient, high conductivity etc, and to structurally modify the system so that it is possible to polymerise it. If functional groups are incorporated that will polymerise, it will become possible to create a three dimensional network or plastic that will have properties associated with the parent organic system.

The advantages of the compounds of the invention is that they allow for the possibility that they can be applied in the form of a paint and caused to polymerise in situ. Thus this allows for ease of processing. Further, by providing for the construction of networks as a result of the cross linking, the resultant polymer can be mechanically strong and durable.

The versatility of the systems of the.invention mean that it is possible to build in anisotropy which would improve directional physical properties, eg NLO, mechanical yield strength etc.

Both amorphous or ordered systems can be prepared depending upon the particular polymerisation conditions used. Copolymerisation is also possible which can be used advantageously to affect physical properties of the polymer obtained.

Systems can be prepared which mimic conventional polymers/elastomers, or which involve donor/acceptor systems.

Polymers of the invention are particularly suitable for the production of adhesive coatings, and multilayer coatings as well as binders. It is possible to manipulate the low molar mass coating before polymerisation is carried out, eg, poling etc.

Films of polymeric material can be prepared as illustrated hereinafter. Thus material with the properties of for example, polyethylene films can be produced using radiation curing techniques if required.

Polymer coatings prepared as described herein have useful water-proofing, corrosion resistance and general dust and dirt protective properties, in particular where they include halogenated and particularly fluorinated bridging groups. Thus they may be used in the production of fabrics such as clothing, electrical components or devices, mechanical components as well as building materials which require this feature. In addition, coatings of this type may produce anti-icing features which are useful, particularly where these materials are exposed to harsh external conditions. Products treated in this way also exhibit strong pearling qualities and this assists in the rapid shedding of condensate. Thus surfaces remain relatively free of such condensates.

Such surfaces can be achieved on at least part of the internal surfaces of a structure containing interconnecting intersitial spaces, such as fibrous or granular material.

The present invention provides a product selected from a fabric, an electrical component or device, a mechanical component, or a construction or building material, having deposited thereon a polymeric coating derived from a monomer of formula (IA) as defined above.

Suitable electrical components include small electrical components such as resistors, capacitors, condensers, circuit breakers, switches and connectors, as well as small assemblies of these, for example circuit boards on which these and/or other components are mounted. Electrical devices include conductors, such as HT leads for example, those used in automobile engines, and cables such as external or underground power cables. Such cables may be pre-coated with plastics of another insulating material.

Plastics coatings in accordance with the invention may be applied to electrical wiring. In particular, monomers of formula (IA) or (IB) which mimic polypropylene would be useful in this context.

Mechanical components include housings, bearings, shafts, gears, wheels, gaskets, filter housing, engines, gearboxes, transmission, steering or suspension components.

Building materials include wood, brick, concrete slabs or other preformed concrete structures, building blocks, stone, slates or insulation materials where there is a possibility that corrosion, weathering or water penetration is likely to cause problems.

Polymer coatings formed in accordance with the invention may be useful in electronic components which have a polymeric coating as resistance layers. The nature of the bridging group $R^{16}$ will affect the resistance of the polymer layer.

Optionally the bridging group $R^1$ may be aromatic or heteroaromatic, i.e. it may include one or more unsaturated carbon rings, optionally containing heteroatoms such as nitrogen, oxygen or sulphur, which give the surface formed additional resistance to etching by plasma etch processes as used in the semiconductor integrated circuit industry.

If necessary, the coating may be discontinuous, for example, patterned by etching, optionally after masking certain areas, so as to provide the desired electronic properties. Techniques for achieving this are well known, and include for example, irradiation with high energy radiation such as electron beams, X-rays or deep ultraviolet rays.

The irradiation breaks the bonds in the polymer and exposed areas can then be dissolved in a developer liquid. Optionally, the coating may consist of a mixture of a monomer and a chemical designed to enhance its sensitivity to radiation exposure during the patterning process, such as quinione diazide or anthraquinone.

Suitable electronic components include printed circuit boards, semiconductor elements, optical devices, videodiscs, compact discs, floppy discs and the like.

The invention will now be particularly described by way of example with reference to the accompanying diagrammatic drawings in which:

FIG. 1 illustrates the way in which compounds of the invention may cyclopolymerise; and FIG. 2 illustrates the production of a network polymer in accordance with the invention:

EXAMPLE 1

Preparation and Polymerisation of Compound No. 1 in Table 2

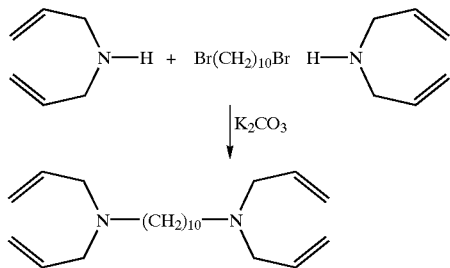

Diallylamine (6.45 g, 0.66 mol), 1,10-dibromodecane (10.0 g, 0.033 mol) and potassium carbonate 9.70 g, 0.66 mol) were placed in ethanol (60 cm$^3$) and the mixture was refluxed for 10 hours. The solids were removed by filtration and the solvent removed in vacuo to leave a yellow oil. The oil was purified by column chromatography using silica gel and ethyl acetate to leave, after removal of solvent in vacuo, 9.80 g, 89% of yellow oil.

$^1$HNMR (CDCl$_3$) δ: 1.15–1.30 (m, 12H), 1.35–1.45 (m, 4H), 2.40 (t, 4H), 3.10 (d, 8H), 5.05–5.20 (m, 8H), 5.30–5.55 (m, 4H). Ir vmax (thin film): 2920, 2850, 2800, 1640, 1460, 1440, 1350, 1250, 1150, 1110, 990, 915 cm$^{-1}$.

Step 2

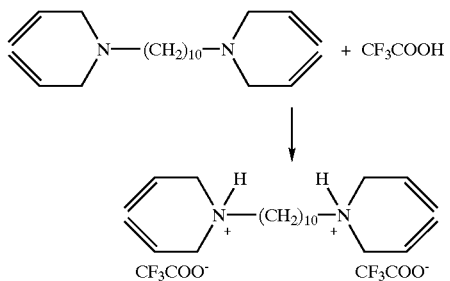

The monomer from step 1 above (4.0 g) was treated with 3M aqueous methanolic trifluoroacetic acid to pH 1.0. The organic phase was extracted with dichloromethane (100 cm$^3$) and washed with brine (60 cm$^3$) and water (60 cm$^3$) and then dried over MgSO$_4$. Removal of solvent left a yellow oil. 6.4 g, 95%.

$^1$HNMR (CDCl$_3$) δ: 1.30 (m, 12H), 1.65 (quin, 4H), 3.0 (quin, 4H), 3.72 (s, 8H), 5.60 (m, 8H), 5.90 (m, 4H), 10.10 (s, 2H). Ir vmax (KCl disc): 2934, 2861, 1780, 1669, 1428, 1169.3(s), 994.5, 950.8, 798, 722, 706, 617 cm$^{-1}$.

Step 3

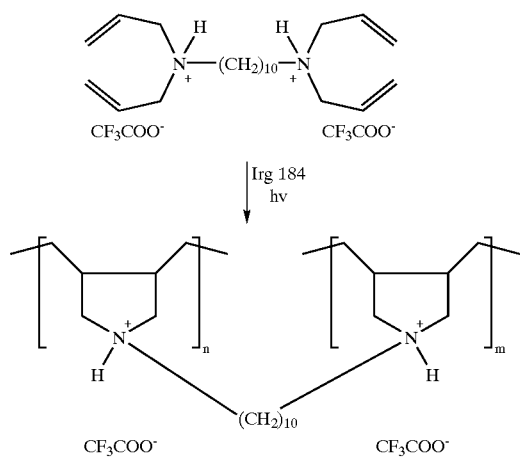

The monomer from step 2 above (0.2 g) and Irgacure 184 (5 mg) were dissolved in dry dichloromethane (2 cm$^3$) and the solution was spread evenly on a 18×25 cm glass plate. The solvent was evaporated off to leave a thin film. It was then irradiated with a Philips UVA sunlamp (75 w) for 10 minutes. The resultant cross-linked polymer was removed as strips (scalpel), washed in dichloromethane (50 cm$^3$) and thoroughly dried. Yield 0.1 g, 50%.

Ir vmax (KCl disc): 2940, 2864, 1780, 1650, 1428, 1170, 995, 951, 799, 743, 722, 620 cm$^{-1}$.

EXAMPLE 2

Preparation and Polymerisation of Compound No. 2 in Table 2
Step 1

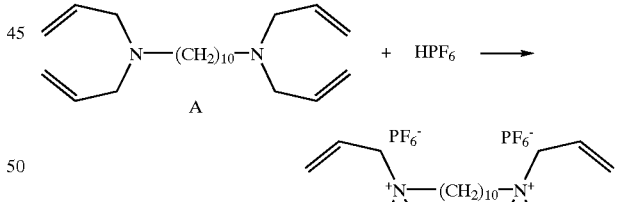

The monomer obtained in Example 1 step 1 (5.0 g) was treated with a 3M aqueous methanolic solution of hexafluorophosphoric acid (3.0 m) to pH1. The PF$_6^-$ salt was extracted using dichloromethane (2×100 cm$^3$) and the combined extracts were dried over MgSO$_4$. Removal of solvent left a yellow oil. 9.16 g, 96%.

Ir vmax (KCl disc) 3508, 3199, 2931, 2859, 2663, 1691, 1648, 1469, 1427, 1290, 1142, 1049, 996, 953, 842.6(s), 737 cm$^{-1}$; $^1$HNMR (CDCl$_3$) δ: 1.25 (s, br, 12H), 1.65 (s, br, 4H), 2.95 (s, br, 4H), 3.65 (s, br, 8H), 5.60 (m, 8H), 5.90 (m, 4H), 9.75 (s, br, 2H).

Step 2

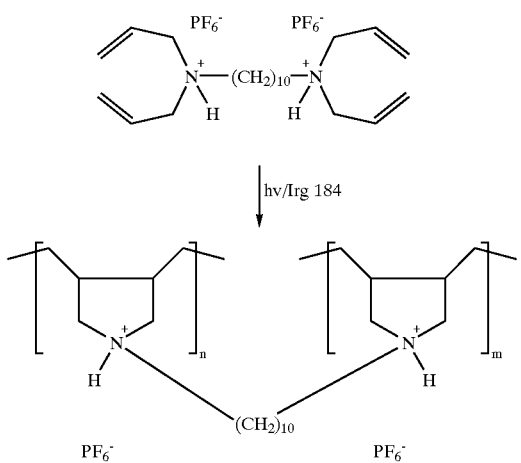

↓ hv/Irg 184

The monomer from step 1 (0.2 g) was dissolved with Irgacure 184 (5 mg) in dry dichloromethane (1.0 cm$^3$) and the solution spread evenly on a 2×4 sq" sheet of aluminium. The solvent was removed by warming and the film was irradiated with the Philips UVA (75 w) u/v lamp for 10 minutes to form a cross-linked polymeric coating.

Ir vmax: 3434, 2937, 2859, 2717, 1674, 1467, 1297, 1140, 843(s) (P-F), 558 cm$^{-1}$.

EXAMPLE 3

Preparation and Polymerisation of Compound No. 3 in Table 2
Step 1

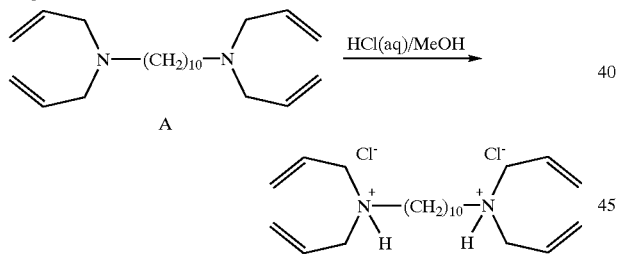

The monomer from Example 1 step 1 (1.0 g) was treated with 3M aqueous methanolic hydrochloric acid to pH 1.0 (universal indicator paper). The organic phase was extracted with dichloromethane (100 cm$^3$) and washed with brine (60 cm$^3$) then water (60 cm$^3$) and dried over MgSO$_4$. Removal of solvent left a heavy yellow oil. 1.2 g, 96%.

Ir vmax (KCl. Disc): 2929, 2855, 2632, 2536, 1645, 1456, 1426, 1362, 1222, 997, 948 cm$^{-1}$; $^1$HNMR (DMSO) δ: 1.25 (m, 10H), 1.67 (m, 4H), 2.89 (m, 4H), 3.66 (s, 8H), 5.42–5.53 (m, 8H), 5.96–6.01 (m, 4H), 11.20 (s, 2H).

Step 2

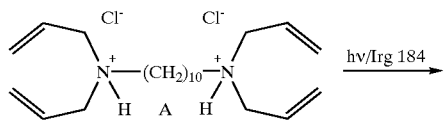

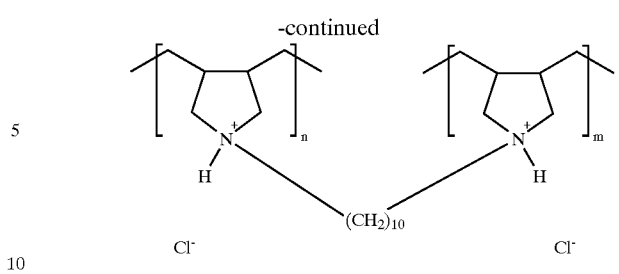

The diallylamine salt obtained in step 1 above (1.0 g, 0.0025 mol) and Irgacure 184 (25.3 mg, 0.000124 mol) were dissolved in dry dichloromethane (2 cm$^3$) and the solution spread on an 18×25 cm$^2$ glass plate. The solvent was allowed to evaporate and the remaining clear film was irradiated for approximately 3 minutes under a Philips UVA (75 w) sunlamp. The resultant cross-linked polymer was removed from the glass plate, washed in dichloromethane and dried. Yield 0.75 g, 75%.

Ir vmax (KCl disc): 2800–2200 (broad), 1620(w), 1455 (s), 1050(w), 1000(w), 950(w), 720(w) cm$^{-1}$.

EXAMPLE 4

Preparation and Polymerisation of Compound No. 4 in Table 2
Step 1

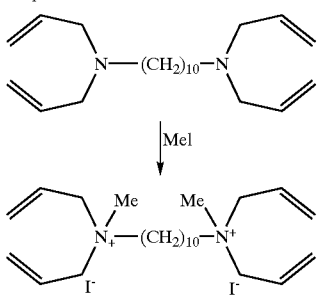

The monomer obtained as described in Example 1 step 1 (3.0 g, 0.0094 mol) and methyl iodide (2.60 g, 0.22 mol) in dry dichloromethane (30 cm$^3$) were refluxed together for 7 hours. The solvent and residual methyl iodide were removed in vacuo and the orange residue re-dissolved in dry dichloromethane (100 cm$^3$). The orange solution was washed in brine (50 cm$^3$) and dried over MgSO$_4$. Removal of solvent gave an orange oil which formed a soft solid on standing. Yield 4.95 g, 89%.

$^1$HNMR (DMSO) δ: 1.27 (m, 12H), 1.69 (m, 4H), 2.99 (6H), 3.10–3.20 (m, 4H), 3.95 (d, 8H), 5.55–5.75 (m, 8H), 5.95–6.18 (m, 4H). Ir vmax (KCl disc): 3081, 2925, 2854, 2361, 1689, 1641, 1470, 1424, 1371, 1302, 1246, 994, 943, 894, 868, 724, 668.

Step 1A

In an alternative preparation of the compound of step 1 above, the monomer obtained as described in Example 1 step 1 above (10.0 g, 0.030 mol) and methyl iodide (9.23 g, 0.065 mol) in a mixture of tetrahydrofuran (100 cm$^3$) and dichloromethane (20 cm$^3$) were stirred together. After 0.5 hours the solution began to become turbid and the turbidity increased as time progressed. The solvent was removed in vacuo and the white solid residue was suspended in 40/60 petrol (100 cm$^3$) and stirred for 1 hour. Filtration and thorough drying in vacuo gave 17.79 g, 96% of white, soft solid.

$^1$HNMR (CDCl$_2$) δ: 1.20–1.40 (s, 12H), 1.80 (s, 4H), 3.20 (s, 6H), 3.40 (m, 4H), 4.15 (m, 8H), 5.65–5.86 (m, 8H), 5.95–6.10 (m, 4H); Ir νmax (KCl disc): 3080, 3050, 2930, 2860, 1640, 1470, 1440, 1425, 1370, 1300, 995, 945 cm$^{-1}$.

Step 2

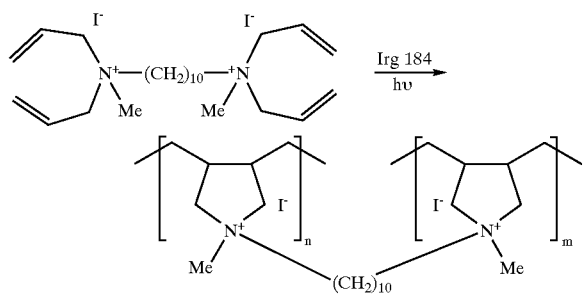

The monomer from step 1 above (0.7 g, 0.00114 mol) and Irgacure 184 (23.2 mg, 0.00014 mol) were dissolved in dry dichloromethane (3 cm$^3$). The monomer/photoinitiator mixture was spread evenly on an 18×25 cm$^3$ glass plate and the solvent left to evaporate in air to leave a clear, light yellow film. The film was irradiated with a Philips UVA (75 w) sunlamp for 15 minutes. Examination showed that the monomer had polymerised to form a hard, cross-linked polymer. The polymer was removed as strips of clear film and placed in dry dichloromethane (100 cm$^3$) and the mixture stirred for 15 minutes. The film strips were removed by filtration and dried in vacuo.

Ir νmax (KCl disc): 2923, 2852, 1680(w), 1613, 1461(s), 950(s), 726 cm$^{-1}$.

A similar reaction using 1.0 g (0.0016 mol) of the monomer obtained in step 1A above and 16.3 g (0.00008 mol) Irgacure 184 produced 0.84 g (84%) of cross-linked polymer.

Ir νmax (KCl disc): 3480 (H$_2$O), 2920, 2860, 1640(w), 1460, 1000, 955 cm$^{-1}$.

EXAMPLE 5

Preparation and Polymerisation of Compound No. 5 in Table 2

Step 1

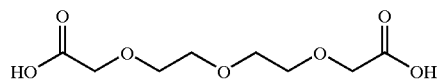

3,6,9-Trioxaundecandioic Acid (4.4 g, 0.0179 mol), 1,4-pentadien-3-ol (3.0 g, 0.0357 mol), 1,3-dicyclohexylcarbodiimide (7.63 g, 0.037 mol) and 4-dimethylaminopyridine (250 mg) were stirred together in dry dichloromethane (100 cm$^3$) for 48 hours at room temperature. The 1,3-dicyclohexylurea was removed by filtration and the solvent removed in vacuo to leave an oil. Purification using silica gel and ethyl acetate—40:60 petrol (1:1) as eluent followed by removal of solvent and thorough drying gave 6.4 g, 91% of colourless, clear oil.

Ir νmax (thin film): 2920, 2860, 1750, 1635, 1420, 1380, 1350, 1270, 1250, 1195, 1150, 1120, 990, 935, 880, 850, 730, 690, 580 cm$^{-1}$; $^1$HNMR (CDCl$_3$) δ: 3.65–3.80 (m, 8H), 4.15 (s, 4H), 5.25–5.50 (m, 10H), 5.75–5.95 (m, 4H).

Step 2

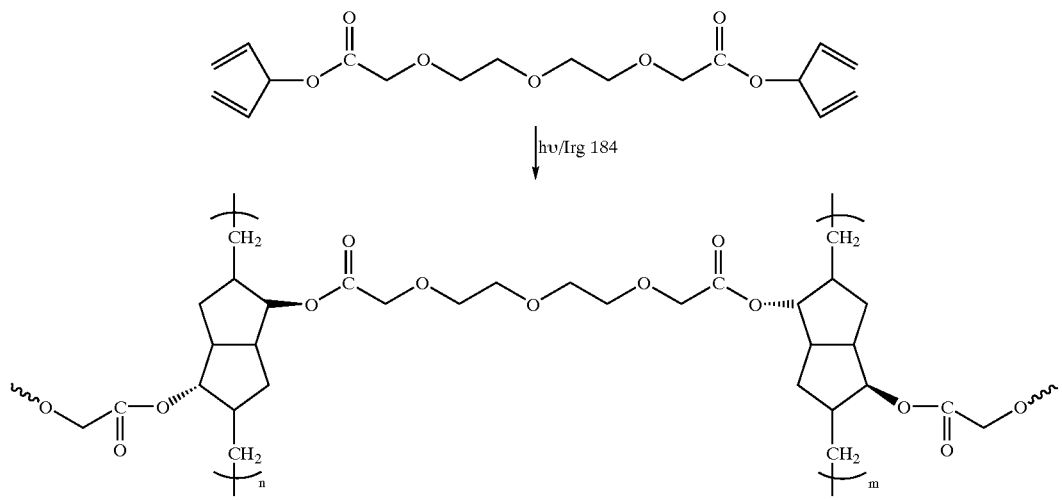

The monomer from Example 5 step 1 (1.5 g, 0.0042 mol) and Irgacure 184 (43 mg) were dissolved in dry dichloromethane (2 ml) and the solution was spread evenly on an 18×25 cm plate glass sheet. The solvent was allowed to dry in air then the remaining polymer/photoinitiator film was irradiated beneath a Philips UVA (70 w) U/V sunlamp for 2 hours. The resultant cross-linked polymer was scraped (scalpel) from the plate and suspended.in. dry dichloromethane (20 ml ) and the suspension was stirred for approximately 15 minutes. The polymer was recovered by filtration and the retained solid washed with dry dichloromethane (2×10 cm³) and then dried thoroughly to leave 0.6 g 40% of clear film polymeric material.

Ir vmax (thin film): 2920, 2860, 1740, 1630, 1450, 1380, 1275, 1200, 1145, 1120, 850 cm$^{-1}$.

EXAMPLE 6

Preparation and Polymerisation of Compound No. 6 in Table 2
Step 1

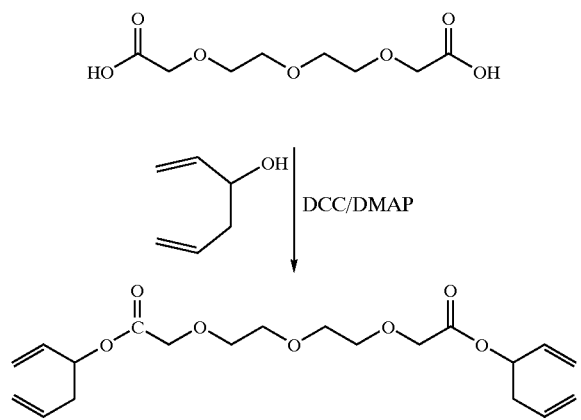

3,6,9-Trioxaundecandioic acid (5.33 g, 0.024 mol), 1,5-hexadien-3-ol (5.0 g, 0.51 mol), 1,3-dicyclohexylcarbodiimide (10.5 g, 0.051 mol) and 4-dimethylaminopyridine (250 mg) were stirred together in dry dichloromethane (50 cm) at room temperature for 6 hours. The 1,3-dicyclohexylurea was removed by filtration and the solvent removed in vacuo to leave a yellow oil which was purified by column chromatography using silica gel/ethyl acetate. Yield 8.0 g, 87%.

$^{1}$HNMR (CDCl$_{3}$) δ: 2.4 (t, 4H), 3.65 (m, 8H), 4.20 (s, 4H), 5.05–5.45 (m, 10H), 5.65–5.90 (m, 4H); Ir vmax (thin film): 2920, 2860, 1760, 1640, 1425, 1200, 1150, 1120, 990, 920 cm$^{-1}$.

Step 2

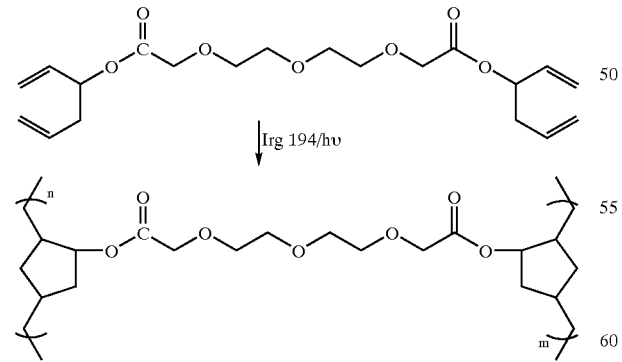

The monomer from step 1 above (1.6 g, 0.0042 mol) and Irgacure 184 (43 mg, 5 mol %) were dissolved in dry dichloromethane (2 ml) and the solution was spread evenly on an 18×25 cm plate glass sheet. The solvent was allowed to dry in air then the remaining polymer/photoinitiator film was irradiated beneath a Philips UVA (70 w) U/V sunlamp for 2 hours. The resultant cross-linked polymer was scraped (scalpel) from the plate land suspended in dry dichloromethane (20 ml) and the suspension was stirred for approximately 15 minutes. The polymer was recovered by filtration and the retained solid washed with dry dichloromethane (2×10 cm³) and then dried thoroughly to leave a clear film polymeric material. Yield 1.34 g, 87%.

Ir vmax (thin film): 2920, 2860, 1740(S), 1635, 1450, 1430, 1380, 1280, 1200, 1145, 1120, 990, 925, 850 cm$^{-1}$.

EXAMPLE 7

Preparation and Polymerisation of Compound No. 7 in Table 2
Step 1

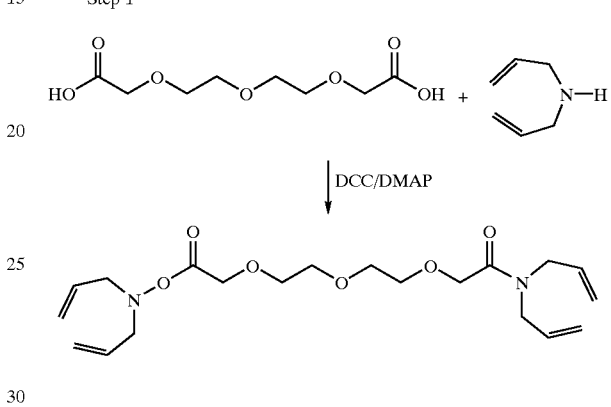

3,6,9-Trioxaundecanoic acid (5.0 g, 0.026 mol), diallylamine (5.10 g, 0.055 mol), 1,3-dicyclohexylcarbodiimide (11.35 g, 0.055 mol) and 4-dimethylaminopyridine (0.5 g) were stirred together in dry dichloromethane (100 cm³) for 6 hours. The resultant 1,3-dicyclohexylurea was removed by filtration and the solvent removed in vacuo to give a yellow oil. Column chromatography using ethyl acetate—petrol 40/60 (1:1) followed by removal of solvent in vacuo and thorough drying gave the product as a yellow oil. (Yield 8.0 g, 94%)

Ir vmax (thin film): 2930, 2860, 1660(s), 1530, 1470, 1450, 1420, 1350, 1280, 1230, 1195, 1115(s), 995, 930, 755 cm$^{-1}$; $^{1}$HNMR (CDCl$_{3}$) δ: 3.70 (m, 8H), 3.90 (m, 4H), 4.0 (m, 4H), 4.25 (s, 4H), 5.10–5.25 (m, 8H), 5.75–5.90 (m, 4H).

Step 2

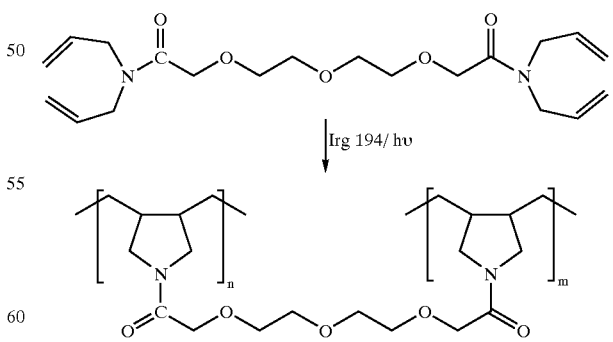

Monomer from step 1 above (1.0 g, 0.00263 mol) and 5 mol % Irgacure 184 (27 mg, 0.00013 mol) were dissolved in dry dichloromethane (3 cm³) and the solution spread over an 18×25 cm glass plate. The solvent was allowed to evaporate to leave a thin clear film. The film was then irradiated with

EXAMPLE 8

Preparation and Polymerisation of Compound No. 8 in Table 2

Step 1

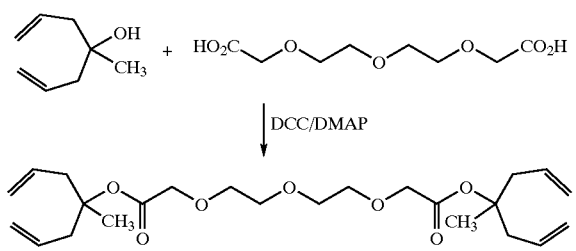

3,6,9-Trioxaundecandioic acid (2.64 g, 0.012 mol), 1,1-diallylethanol (3.0 g, 0.023 mol), 1,3-dicyclohexylcarbodiimide (5.16 g, 0.025 mol) and 4-dimethylaminopyridine (150 mg) were dissolved in dry dichloromethane (100 cm$^3$) and the solution stirred for 18 h at room temperature. 1,3-Dicyclohexylurea was removed by filtration and the solvent removed in vacuo to leave a yellow oil. Column chromatography using silica gel and ethyl acetate gave, after removal of solvent in vacuo, a clear oil, 4.9 g, 94%.

$^1$HNMR (CDCl$_3$) δ 1.45 (s, 8H), 2.50–2.70 (m, A:B, 8H), 3.70 (s, 6H), 4.05 (s, 4H), 5.05–5.15 (m, 8H), 5.70–5.90 (m, 4H); Ir νmax (thin film): 2920, 2870, 1750, 1450, 1380, 1210, 1150, 1120, 740, 700 cm$^{-1}$.

Step 2

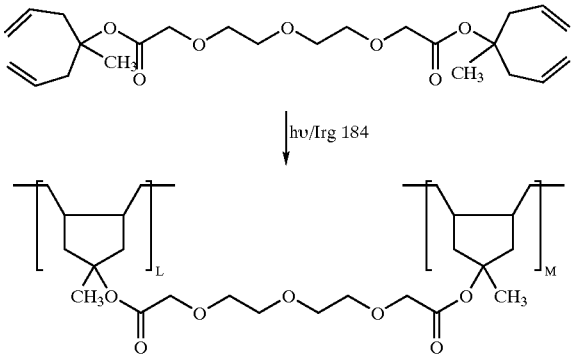

The monomer from Step 1 above (1.0 g, 0.0023 mol) and Irgacure 184 (5 mol %; 23.5 mg, 0.00012 mol) were dissolved in dry dichloromethane (3 cm$^3$) and the solution spread over a 18×25 cm glass plate. The solvent was allowed to evaporate to leave a thin clear film. The film was them irradiated with a Philips UVA sunlamp (75 w) to form a hard cross-linked polymer coating. The coating was removed and washed in dry dichloromethane and then dried thoroughly. Yield 0.78 g, 78%.

Ir νmax (KCl disc): 2940, 2880, 1750, 1450, 1380, 1205, 1145, 1120, 1030, 960 cm$^{-1}$.

EXAMPLE 9

Preparation and Polymerisation of Compound No. 9 in Table 2

Step 1

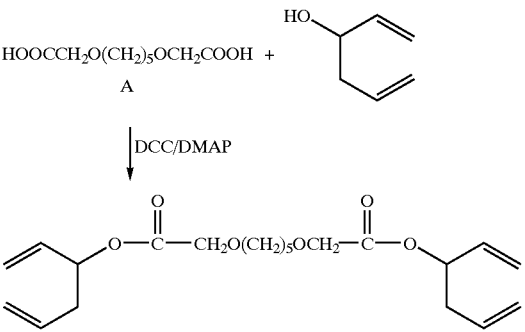

The diacid illustrated above (2.5 g, 0.0114 mol), 1,5-hexadien-3-ol (1.34 g, 0.024 mol), 1,3-dicyclohexylcarbodiimide (206.33) (5.16 g, 0.025 mol) and 4-dimethylaminopyridine (200 mg) were placed in dry dichloromethane (100 cm$^3$) and the solution stirred for 18 hours at room temperature. 1,3-dicyclohexylurea was removed by filtration and the solvent removed in vacuo to leave a yellow oil. Column chromatography using silica gel with ethyl acetate gave a clear oil, 2.84 g, 66%.

$^1$HNMR (CDCl$_3$) δ 1.20 (quin, 2H), 1.65 (m 4H), 2.40 (t, 4H), 3.60 (d, 4H), 4.20 (s, 4H), 5.05–5.45 (m, 10H), 5.65–5.90 (m, 4H). Ir νmax (thin film): 2920, 2860, 1750, 1700, 1510, 1430, 1240, 1200, 1140, 1030, 990, 920, 760 cm$^{-1}$.

Step 2

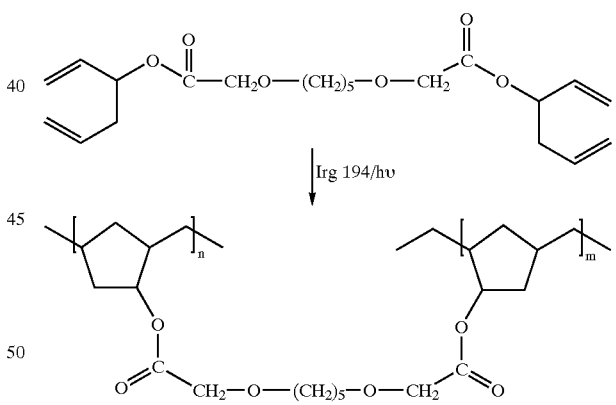

Monomer from step 1 above (0.7 g, 0.001894 mol) and Irgacure 184 (37.6 mg, 0.0000184 mol) were dissolved in dry dichloromethane (3 cm$^3$) and the solution was spread on an 18×25 cm$^3$ glass plate. The solvent was allowed to evaporate to leave a clear film. This was irradiated with a Philips UVA (75 w) sunlamp for 2 hours until the film hardened. The film was removed and placed in dry dichloromethane (50 cm$^3$) and stirred for 1 hour. The cross-linked polymer was removed by filtration and washed with dry dichloromethane (2×50 cm$^3$) and dried thoroughly to leave a creamy coloured polymeric solid. Yield 0.35 g, 50%.

Ir νmax (KCl disc): 2940, 2860, 1750(s), 1450, 1285, 1205, 1130, 1030 cm$^{-1}$.

EXAMPLE 10

Preparation and Polymerisation of Compound No. 10 in Table 2

Step 1

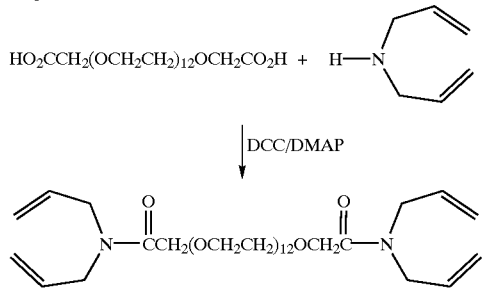

Polyethylene glycol 600 diacid (12.0 g, 0.020 mol), diallylamine (4.67 g, 0.048 mol), 1,3-dicyclohexylcarbodiimide (10.6 g, 0.048 mol) and 4-dimethylaminopyridine (600 mg) were placed in dichloromethane (100 cm$^3$) and the mixture stirred for 24 hours at room temperature. The 1,3-dicyclohexylurea was removed by filtration and the solvent removed in vacuo to leave a yellow oil. Column chromatography (silica gel/ethyl acetate) followed by removal of solvent in vacuo gave a pale yellow oil. 13.90 g, 92%.

$^1$HNMR (CDCl$_3$) δ: 3.60 (m, 48H), 3.90 (d, 4H), 4.0 (d, 4H), 4.20 (s, 4H); 5.15 (m, 8H), 5.75 (m, 4H). Ir vmax (thin film): 3016, 2922, 1662(s), 1470, 1353, 1219, 1114, 931, 756, 666 cm$^{-1}$.

Step 2

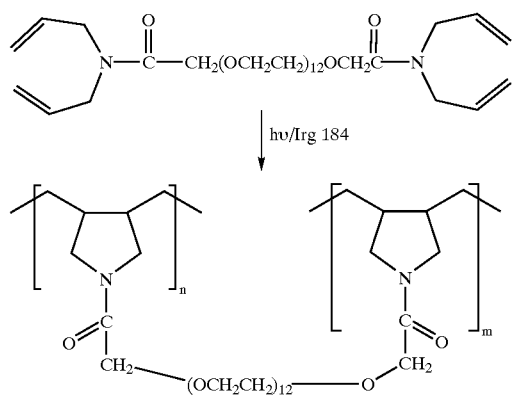

Monomer from Step 1 (1.0 g) and Irgacure (1.5 mg) were dissolved in dry dichloromethane (3 cm$^3$) and thoroughly mixed. The solution was spread evenly on, an 18×25 cm glass plate and the solvent allowed to evaporate to leave a thin film of monomer. The film was irradiated with the Philips UVA (75 w) sunlamp for 30 minutes to form a soft, permeable to water, cross-linked polymer film.

Ir vmax (thin film): 3438, 2946, 2371, 1703, 1648(s), 1544, 1510, 1457, 1352, 1099(vs), 953, 856, 727, 551 cm$^{-1}$.

EXAMPLE 11

Preparation and Polymerisation of Compound No. 11 in Table 2

Step 1

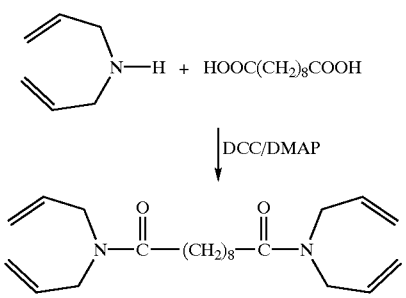

Diallylamine (9.72 g, 0.1 mol), sebacic acid (10.00 g, 0.0050 mol), 1,3-dicyclohexylcarbodiimide (22.70 g. 0.11 mol) and 4-dimethylaminopyridine (0.450 g) were stirred together in dry dichloromethane (100 cm$^3$) for 6 hours. The resultant 1,3-dicyclohexylurea was removed by filtration and the solvent removed in vacuo to give a yellow oil. Column chromatography using ethyl acetate—petrol 40/60 (1:1) followed by removal of solvent in vacuo and thorough drying gave the product as a yellow oil. 15.90 g, 90%.

Ir vmax (thin film): 2920, 2850, 1690(w), 1640(s), 1520, 1460, 1410, 1220, 990, 920, 730 cm$^{-1}$; $^1$HNMR (CDCl$_3$) δ: 1.10–1.45 (m, 6H), 1.50–2.00 (m, 6H), 2.40 (t, 4H), 3.90 (d, 4H), 4.0 (d, 4H), 5.05–5.20 (m, 8H), 5.20–5.90 (m, 4H).

Step 2

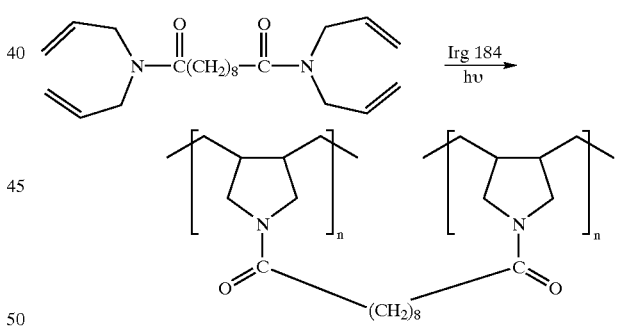

Monomer from Step 1 (1.00 g, 0.0028 mol) and Irgacure 184 (28.3 mg, 0.000139 mol) were dissolved in dry dichloromethane (3 cm$^3$) and the solution spread over a 18×25 cm glass plate. The solvent was allowed to evaporate to leave a thin clear film. The film was then irradiated with a Philips UVA sunlamp (75 w) for approximately 5 minutes to form a hard polymeric cross-linked coating. The coating was removed and washed in dry dichloromethane and then thoroughly dried. Yield 0.80 g, 80%.

Ir vmax KCl disc): 2920, 2860, 1640, 1530, 1450, 1230 (w), 1340(w), 1230(w), 1000(w), 930(w).

EXAMPLE 12

Preparation and Polymerisation of Compound No. 12 in Table 2

Step 1

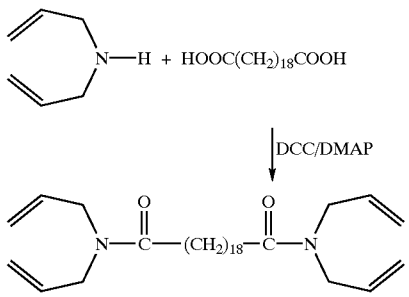

Eicosanedioic acid (5.0 g, 0.0146 mol), diallylamine (3.12 g, 0.032 mol), 1,3-dicyclohexylcarbodiimide (6.60 g, 0.032 mol) and 4-dimethylaminopyridine (200 mg) were dissolved in dichloromethane/tetrahydrofuran mixture (1:1) (100 cm$^3$) and the mixture stirred at room temperature for 72 hours. 1,3-Dicyclohexylurea was removed by filtration and the solvent removed in vacuo to leave a yellow oil. Column chromatography using silica gel/ethyl acetate followed by removal of solvent in vacuo and thorough drying gave a pale yellow oil. 6.35 g, 87%.

$^1$HNMR (CDCl$_3$) δ: 1.20 (s, br, 28H), 1.60 (m, 4H), 1.80 (m, 4H), 3.90 (d, 4H), 4.0 (d, 4H), 5.10 (m, 8H), 5.75 (m, 4H). Ir νmax (thin film): 3006, 2927, 2854, 1643, 1530, 1466, 1415, 1217, 1084, 992, 925, 893, 756, 666 cm$^{-1}$.

Step 2

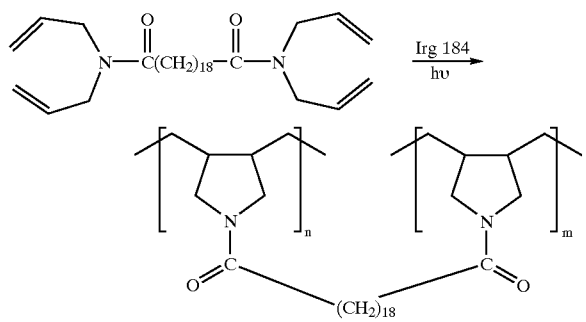

Monomer from Step 1 (0.25 g) and Irgacure 184 (5 mg) were dissolved in dry dichloromethane (1.0 cm$^3$) and the solution was heated (water bath) to ensure even distribution of photoinitiator. The solution was spread evenly on a 4×2" piece of aluminium foil and the solvent was allowed to evaporate off to leave a thin film of monomer/photoinitiator. This was irradiated with a Philips UVA (75 w) sunlamp for 30 minutes until a hard cross-linked polymer was formed. To test for hydrophobicity, the foil+polymer was subjected to running water for 30 minutes. After this time the polymer laminate was not adversely affected, i.e. no loss of adhesion to the foil.

Ir νmax (KCl disc): 2924, 2851, 1648, 1534, 1452, 1227, 721 cm$^{-1}$.

EXAMPLE 13

Preparation and Polymerisation of Compound No. 13 in Table 2

Step 1

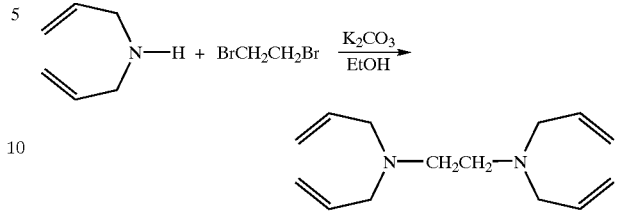

Diallylamine (12.90 g, 0.132 mol), 1,2-dibromoethane (12.40 g, 0.066 mol) and potassium carbonate (18.80 g, 0.132 mol) were refluxed in ethanol (100 cm$^3$) for 24 hours. Solids were removed by filtration and solvents removed in vacuo to leave a yellow oil. The oil was purified by column chromatography (silica gel/ethyl acetate) to leave a pale yellow oil. 13.40, 92%.

$^1$HNMR (CDCl$_3$) δ: 2.55 (s, 4H), 3.10 (d, 8H), 5.10 (m, 8H), 5.80 (m, 4H); Ir νmax (thin film): 3082, 3012, 2983, 2927, 2806, 1645, 1447, 1420, 1355, 1262, 1109, 997, 919, 559 cm$^{-1}$.

Step 2

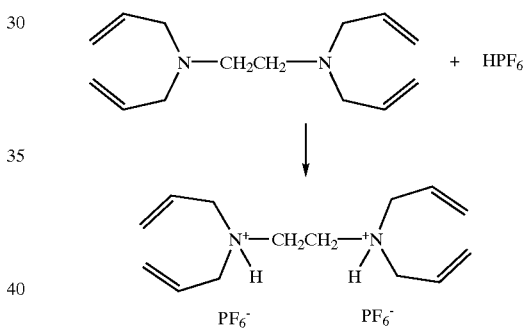

Monomer from Step 1 (5.0 g) was treated with an aqueous methanolic solution of hexafluorophosphonic acid 60% solution in H$_2$O (3.0 m) to pH1. The PF$_6$ salt was extracted using dichloromethane (2×100 cm$^3$) and the combined extracts were dried over MgSO$_4$. Removal of solvent left a yellow oil. 8.0 g, 96%.

$^1$HNMR (CDCl$_3$) δ: 3.60 (d, 2H), 3.75 (d, 2H), 3.80 (s, 8H), 5.55 (m, 8H), 5.90 (m, 4H), 9.80 (s, br, 2H); Ir νmax (thin film): 3428, 2986, 2634, 1460, 1426, 1294, 1246, 1142, 1053, 977, 953, 842, 740 cm$^{-1}$.

The product may then be polymerised, for example as described in Example 1 Step 3 above.

EXAMPLE 14

Preparation and Polymerisation of Compound No. 14 in Table 2

Step 1

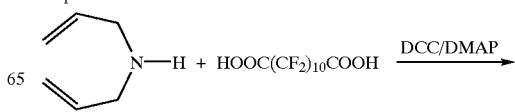

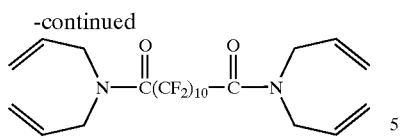

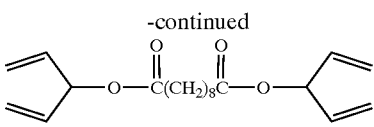

Diallylamine (1.41 g, 0.0145 mol), perfluoro-1,10-decanedicarboxylic acid (2.5 g, 0.0073 mol), 1,3-dicyclohexylcarbodiimide (3.20 g, 0.0155 mol) and 4-dimethylaminopyridine (0.5 g) were stirred together in dry dichloromethane (60 cm$^3$) for 6 hours. The solvent was removed in vacuo to leave a white solid which was purified using column chromatography (ethyl acetate-petrol 40/60 1:1) and dried thoroughly to give 2.96 g, 79% of clear oil.

$^1$HNMR (CDCl$_3$) δ: 3.90 (d, 4H), 4.00 (d, 4H), 5.10–5.25 (m, 8H), 5.70–5.81 (m, 4H); Ir vmax (thin film): 2933, 2857, 1692, 1645.5, 1611.4, 1576, 1454, 1419, 1377, 1350, 1219, 1151, 1081, 992, 932, 892, 735, 657, 556.

Step 2

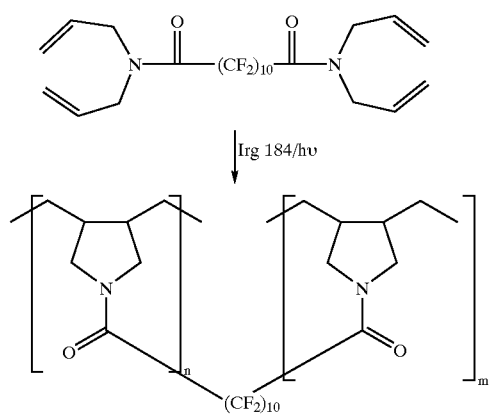

Monomer from Step 1 (1.0 g, 0.0019 mol) was dissolved in dry dichloromethane (3 cm$^3$) and Irgacure 184 (20 mg, 0.000095 mol) and the resultant solution spread evenly over an 18×25 cm glass plate. The solvent was allowed to evaporate off to leave a clear liquid layer of monomer/photoinitiator. The plate was placed under a Philips UVA (75 w) sunlamp for approximately 15 minutes. The resultant clear film was removed (powdery) and dried after stirring for 30 minutes in dry dichloromethane (100 cm$^3$) to leave 0.79 g, 79% of white powder.

Ir vmax (thin film) 2936, 2859, 1691, 1624, 1576, 1455, 1372, 1218, 1151, 1079, 892, 729, 654, 555 cm$^{-1}$.

EXAMPLE 15

Preparation and Polymerisation of Compound No. 15 in Table 2
Step 1

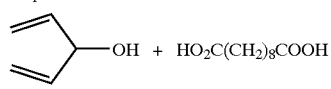

|DCC/DMAP

Sebacic acid (2.0 g, 0.0099 mol), 1,4-pentan-3-ol (1.7 g, 0.02 mol), 1,3-dicyclohexylcarbodiimide (4.52 g, 0.022 mol) and 4-dimethylaminopyridine (200 g) in dry dichloromethane (60 cm$^3$) were stirred together for 18 hours. The 1,3-dicyclohexylurea was removed by filtration and solvent removed to leave clear oil. This was dissolved in 40/60 petrol (100 cm$^3$) and washed in water then dried over MgSO$_4$. Removal of solvent left a clear, colourless oil which tlc (dichloromethane) (developing in iodine) showed as a single spot. The oil was thoroughly dried in vacuo to leave 2.49 g, 75% of clear oil.

$^1$HNMR (CDCl$_3$) δ: 1.30 (s, 8H), 1.60 (t, 4H), 2.35 (t, 4H), 5.15–5.35 (m, 8H), 5.65–5.95 (m, 6H); Ir vmax (thin film): 2920, 2860, 1730, 1640, 1510, 1460, 1410, 1365, 1240, 1165, 1095, 985, 930 cm$^{-1}$.

Step 2

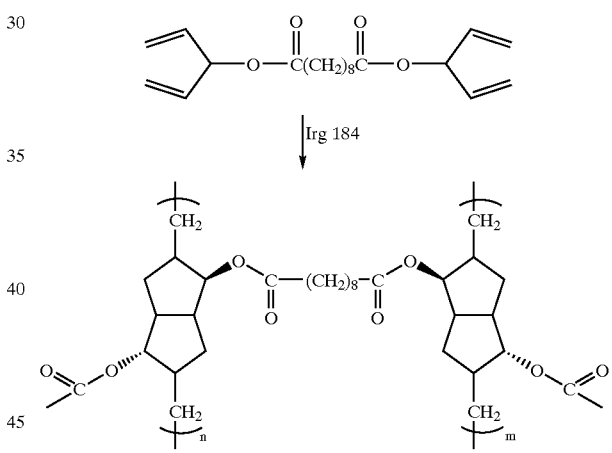

Monomer from Step 1 (1.0 g, 0.003 mol) and Irgacure 184 (31 mg, 0.00015 mol) were dissolved in dry dichloromethane (2 ml) and the solution was spread evenly on an 18×25 cm plate glass sheet. The solvent was allowed to dry in air then the remaining polymer/photoinitiator film was irradiated beneath a Philips UVA (75 w) sunlamp for 2 hours. The resultant cross-linked polymer was scraped (scalpel) from the plate and suspended in dry dichloromethane (20 ml) and the suspension was stirred for approximately 15 minutes. The polymer was recovered by filtration and the retained solid washed with dry dichloromethane (2×10 cm$^3$) and then dried thoroughly to leave 0.85 of clear film polymeric material.

Yield 0.85 g, 85% Ir vmax (thin film): 2920, 2860, 1725, 1520, 1450, 1365, 1240, 1170, 1090, 985 cm$^{-1}$.

EXAMPLE 16

Preparation and Polymerisation of Compound No. 16 in Table 2
Step 1

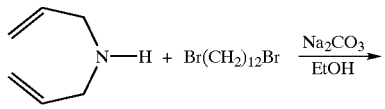

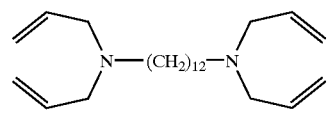

Diallylamine (12.70 g, 0.134 mol), 1,12-dibromododecane (20.0 g, 0.061 mol) and potassium carbonate (18.50 g, 0.134 mol) in ethanol (100 cm³, were refluxed together for 18 hours. The solids were removed by filtration and the solvent removed in vacuo to leave a yellow oil. The oil was passed through a silica gel column using ethyl acetate as the eluent. Removal of solvent in vacuo gave a pale yellow oil which was thoroughly dried. Yield 17.4 g, 79%.

¹HNMR (CDCl₃) δ: 1.20 (m, 16H), 1.45 (t, 4H), 2.40 (t, 4H), 3.10 (d, 8H), 5.05–5.15 (m, 8H), 5.80 (m, 4H); Ir vmax (thin film) 3080, 3020, 2920, 2860, 2800, 1645, 1470, 1420, 1355, 1260, 1155, 1115, 1090, 1000, 920, 725 cm⁻¹.

Step 2

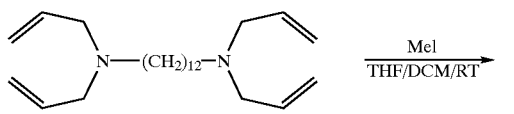

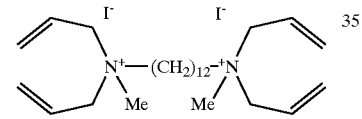

The diamine from step 1 (10.00 g, 0.028 mol) and methyl iodide (8.52 g, 0.060 mol) in a mixture of tetrahydrofuran (100 cm³) and dichloromethane (20 cm³ were stirred together. After 0.5 hours the solution began to become turbid and the turbidity increased as time progressed. The solvent was removed in vacuo and the white solid residue was suspended in 40/60 petrol (100 cm³) and stirred for 1 hour. Filtration and thorough drying in vacuo gave 17.40 g, 97% of white, soft solid.

¹HNMR (CD₂Cl₂) δ: 1.15–1.40 (m, 16H), 1.80 (s, br, 4H), 3.20 (s, 6H), 3.30–3.45 (m, 4H), 4.15 (d, 8H), 5.65–5.90 (m, 8H), 5.95–6.15 (m, 4H); Ir vmax.(thin film): 2920, 2860, 1690, 1640, 1470, 1370, 1300, 1250, 1000, 945 cm⁻¹.

This material could be polymerised as described in previous examples.

EXAMPLE 17

Preparation and Polymerisation of Compound No. 17 in Table 2
Step 1

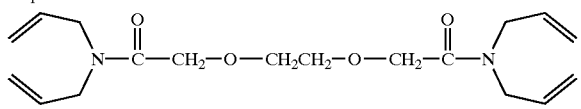

Diallylamine (8.80 g, 0.0090 mol), 3,6-dioxaoctandioic acid (8.00 g, 0.0448 mol) were mixed together as shown in Example 15 Step 1. The mixture was stirred in dichloromethane for 24 hours. The crude product was recovered and purified via silica gel/ethyl acetate to leave a clear oil. Yield 13.43 g, 89%.

¹HNMR (CDCl₃) δ: 3.70 (s, 4H), 3.80 (d, 4H), 3.95 (d, 4H), 4.20 (s, 4H), 5.20 (m, 8H), 5.60 (m, 4H); Ir vmax (thin film) 3080, 2940, 2860, 1650, 1530, 1470, 1420, 1350, 1280, 1235, 1120, 995, 930, 860, 815 cm⁻¹.

Step 2

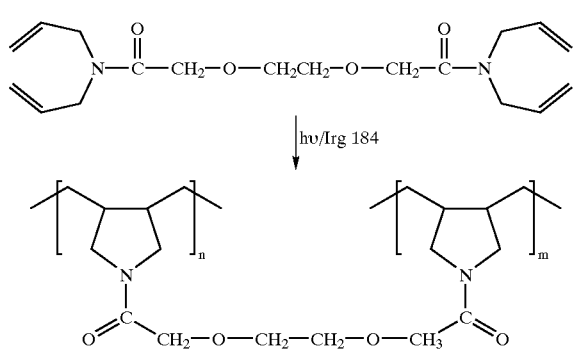

Irgacure 184 (5 mg) as placed in Monomer from Step 1 (0.2 g) and heated to form a clear solution. It was then stirred to ensure complete mixing of photoinitiator then placed on a 1.5 ²in piece of copper (ex DRA) and spread evenly using 100 μm K bar. It was then irradiated for 1 hour beneath a Philips UVA sunlamp and allowed to stand for 24 hours.

Ir vmax (thin film): 2940, 2860, 1640 (strong), 1460, 1345, 1125, 730 cm⁻¹.

EXAMPLE 18

Preparation and Polymerisation of Compound No. 18 in Table 2
Step 1

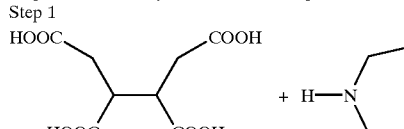

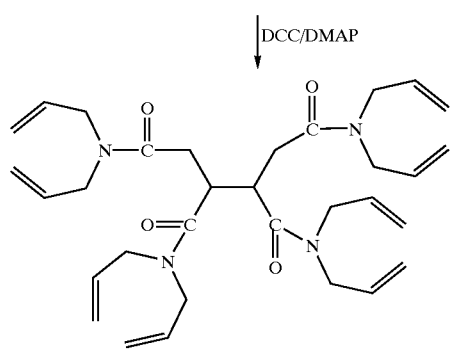

Meso-butan-1,2,3,4-tetracarboxylic acid (20.0 g, 0.0428 mol), diallylamine (39.0 g, 0.20 mol), 1,3-dicyclohexylcarbodiimide (82.50 g, 0.20 mol) and 4-dimethylaminopyridine (2.0 mg) were dissolved in dichloromethane/tetrahydrofuran (1:1) mixture (200 cm³) and the mixture was stirred at room temperature for 120 hours. 1,3-dicyclohexylurea was removed by filtration and the solvent removed in vacuo to leave a yellow oil. Column chromatography (silica gel/ethyl acetate) followed by removal of solvent in vacuo gave a heavy pale yellow oil which solidified on standing. 42.3 g, 89%.

¹HNMR (CDCl₃) δ: 2.90 (m, 4H), 3.50 (m, 2H), 3.80 (m, 16H), 5.20 (m, 16H), 5.70 (m, 8H); Ir vmax (thin film): 3323, 3086, 2935, 2861, 1650, 1545, 1416, 1363, 1228, 1135, 994, 925, 556 cm⁻¹.

Step 2

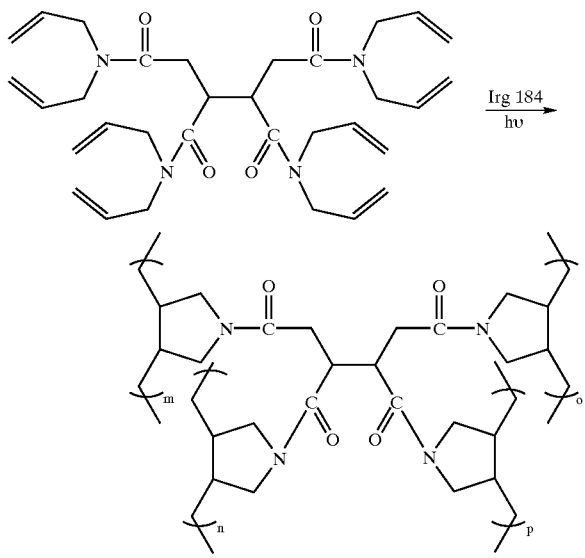

EXAMPLE 19

Preparation and Polymerisation of Compound No. 19 in Table 2

Step 1

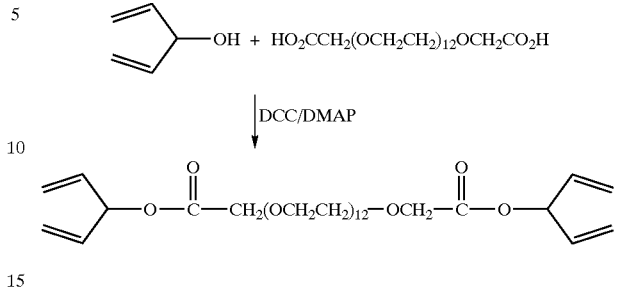

Polyethylene glycol 600 diacid (6.0 g, 0.010 mol), 1,4-pentadiene-3-ol (2.0 g, 0.024 mol) 1,3-dicyclohexylcarbodiimide (206.33) (4.95 g, 0.024 mol) and 4-dimethylaminopyridine (300 mg) were stirred together in dry dichloromethane (50 ml) for 72 h. The resultant 1,3-Dicyclohexyl-urea was removed by filtration and removal of solvent left a clear oil. Column chromatography using silica gel and dichloromethane—40/60 petrol (1:1) followed by dichloromethane-methanol (1:3) gave, after removal of solvent, a colourless, clear oil. 6.73 g, 85%.

¹HNMR (CDCl₃) δ: 3.55–3.80 (m, 48H), 4.15 (s, 4H), 5.25–5.50 (m, 10H), 5.75–5.95 (m, 4H); Ir vmax (thin film): 2860, 1745, 1635, 1450, 1345, 1250, 1195, 1140, 1115, 990, 940, 750 cm⁻¹.

Step 2

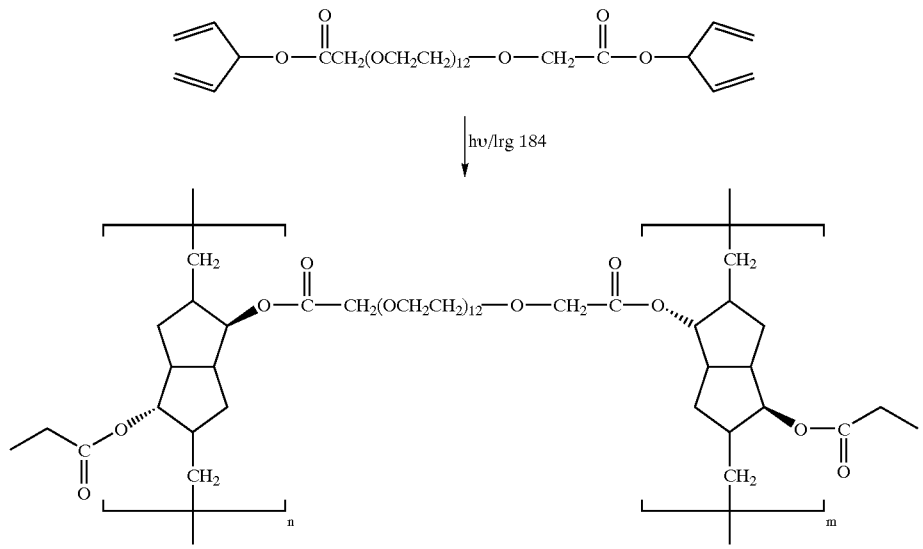

Monomer from Step 1 (1.0 g) was dissolved in dry dichloromethane (3 cm³). The Irgacure 184 (10 mg) was added to the solution, heated and mixed to ensure homogenicity. It was then spread evenly on an 18×25 cm glass plate and the solvent allowed to evaporate off to leave a thin, clear film. This was irradiated with a Philips UVA sunlamp for 30 minutes to form a hard cross-linked polymer film. This was removed (scalpel), washed in dichloromethane and dried. Yield 0.64 g, 64%.

Ir vmax (thin film): 3424, 2936, 2374, 2346, 1705, 1644(s), 1524, 1436(s), 1222, 1138, 992, 924, 561 cm⁻¹.

Monomer from Step 1 (1.6 g, 0.0021 mol) and Irgacure 184 (21 mg, 0.000105 mol) were dissolved in dry dichloromethane (3 cm³) and the solution was spread over a 18×25 cm glass plate. The solvent was allowed to evaporate to leave a thin, clear film. The film was then irradiated with a Philips UVA sunlamp (75 w) to form a hard cross-linked polymer coating. The coating was removed and washed in dry dichloromethane and dried thoroughly.

Yield 1.10 g, 67% Ir vmax (KCl disc): 2920, 2860, 1745, 1680, 1640, 1450, 1345, 1280, 1250, 1200, 1140, 1110, 950, 850 cm⁻¹.

EXAMPLE 20

Preparation of Copolymer

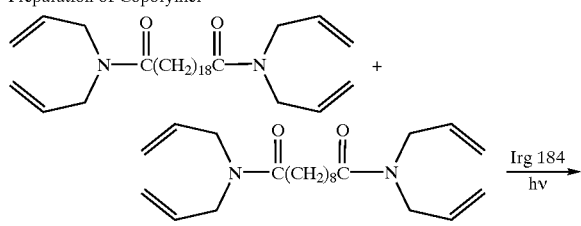

The Monomer of Example 12 Step 1 (0.5 g) and the monomer of Example 11 Step 1, were dissolved with the Irgacure 184 (20 mg) in dichloromethane (5 cm$^3$) and the solution was spread evenly on an 18×25 cm glass plate. The solvent was evaporated off and the residual film irradiated with the Philips UVA (75 w) sunlamp for 1 hour. The resultant cross-linked copolymeric film was removed in strips (scalpel) and washed in dichloromethane, then thoroughly dried. The resultant film was soft, stretchy but of low tensile strength.

Ir vmax (thin film): 3431, 2931, 2858, 1649(s), 1453, 720 cm$^{-1}$.

EXAMPLE 21

Preparation of Copolymer

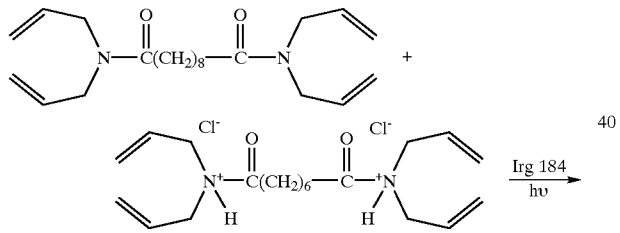

The monomer of Example 11 Step 2 (0.5 g) and compound 30 in Table 2 above (0.5 g) (prepared by analogous methods to those described above), were dissolved in dry dichloromethane (5 cm$^3$). The Irgacure 184 (20 mg) was added and the mixture warmed (water bath) until the photoinitiator had dissolved. The solution was spread evenly on an 18×25 cm glass plate and the solvent allowed to evaporate. The two monomers phase separated to give an even 'pimpled' effect. Attempts to mix the two monomers using dichloromethane and mechanical mixing resulted, after evaporation of solvent, in the same pimpled effect. The monomers were irradiated with the Philips UVA (75 w) sunlamp for 1 hour to form a phase-separated cross-linked solid polymeric 'pimpled' film but unstable due to the discontinuity of polymerisation at each phase boundary.

Ir vmax (thin film): 3421(s), 2939(s9), 1642(s), 1456, 1167, 577 cm$^{-1}$.

EXAMPLE 22

Preparation of Copolymer

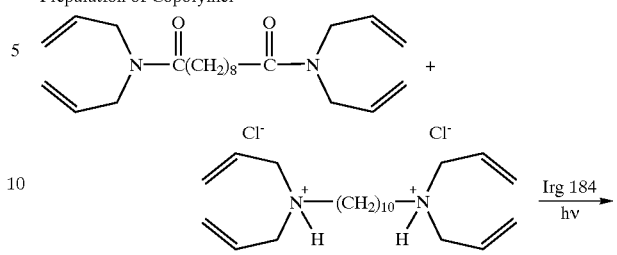

The monomer of Example 11 step 1 (0.5 g) and the monomer of Example 3 Step 2 (0.5 g), were dissolved with the Irgacure 184 (20 mg) in dichloromethane (5 cm$^3$) and the solution was evenly spread on an 18×25 cm glass plate. The solvent was evaporated off to leave a residual clear film which was irradiated with the Philips UVA (75 w) sunlamp for 1 hour. The resultant cross-linked polymer was removed in strips (scalpel) and washed in dichloromethane (50 cm$^3$) then thoroughly dried.

Ir vmax (thin film): 3448(s), 2931, 2855, 1629(s), 1534, 1452, 1230, 731 cm$^{-1}$.

EXAMPLE 23

Other polymerisable monomers were produced as follows:

EXAMPLE 23a

Preparation and Polymerisation of Compound No. 20 in Table 2

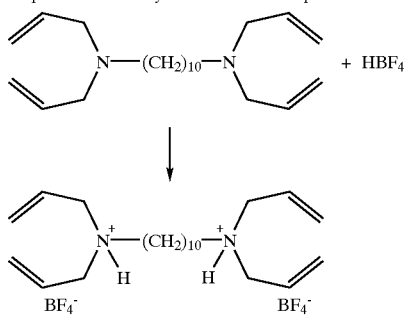

The monomer illustrated (5.0 g) above was treated with a 50% aqueous solution of fluoroboric acid to pH 1.0 (universal indicator paper). The organic phase was extracted using dichloromethane (2×75 cm$^3$) and then dried over MgSO$_4$. Removal of solvent in vacuo gave a heavy pale yellow oil. 7.40 g, 97%.

$^1$HNMR (CDCl$_3$) δ: 1.20 (s, br, 12H), 1.65 (s, br, 4H), 3.05 (quin, 4H), 3.75 (t, 8H), 5.55 (m, 8H), 5.90 (m, 4H), 7.15 (s, br, 2H); Ir vmax (thin film): 3410(br), 2930, 2857, 2649, 1707, 1646, 1460, 1428, 1056.8(very strong), 952, 763 cm$^{-1}$.

EXAMPLE 23b

Preparation and Polymerisation of Compound No. 21 in Table 2

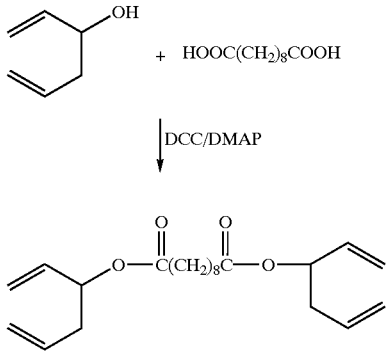

Using the procedure described in Example 23a, sebacic acid (10.06 g, 0.050 mol), 1,5-Hexadiene-3-ol (9.80 g, 0.1 mol), 1,3-dicyclohexylcarbodiimide (22.70 g, 0.11 mol) and 4-dimethylaminopyridine (450 mg) were mixed together to give the desired product Yield: 15.6 g, 87%.

$^1$HNMR (CDCl$_3$) δ: 1.30 (s, 10H), 1.60 (t, 8H), 2.35 (s, 2H), 5.05–5.45 (m, 10H), 5.65–5.90(m, 4H). Ir vmax (thin film): 2920, 2860, 1730, 1640, 1510, 1460, 1410, 1365, 1235, 1160, 1095 cm$^{-1}$.

EXAMPLE 24

Coated Metal Sheets

A photoinitiator (Irgacure 184 or Daracure 1173 supplied by CIBA) was added to Compound 2 in Table 2 of a low permeability polymer in the weight ratio of 5:95. The mixture was then briefly heated to promote mixing before agitation using a cyclone mixer. The monomer mixture was then ready for use. A metal sheet (for example copper or aluminium) was then covered with the mixture either simply by painting the mixture onto the metal surface or via spin-coating. The sheet and mixture was then exposed to UV light to induce polymerisation. Complete polymerisation requires approximately 2 minutes under a high powered (industrial type) broad band UV lamp for a thick (>5 μm) film, or approximately 20 minutes for a similar thickness of film in a standard laboratory UV lamp. The resulting polymer film on the substrate was not removed from the metal surface using a standard tape test.

EXAMPLE 25

Preparation of Compound No. 36 in Table 2

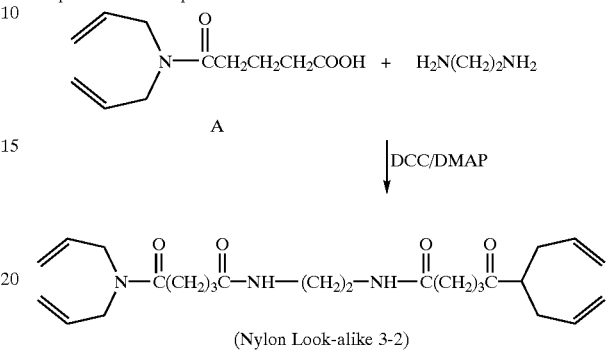

(Nylon Look-alike 3-2)

1,2-Diaminoethane (1.38 g, 0.023 mol) and dicyclohexylcarbodiimide (9.90 g, 0.048 mol) were dissolved in dry dichloromethane (100 cm$^3$). The 4-dimethylaminopyridine (0.50 g) was added followed by amide A (10.0 g, 0.047 mol in 30 cm$^3$ dry dichloromethane) dropwise over 30 minutes and the whole was left stirring for 5 days. The dicyclohexylurea was removed by filtration (Whatman No. 1 filter paper) and the solvent removed in vacuo to leave a yellow oil. Chromatography using silica gel with ethyl acetate followed by methanol as eluents gave, after removal of solvent in vacuo, 9.84 g, 96% of yellow oil.

Ir vmax (thin film): 3307(s), 3088, 2944, 1629, 1550, 1418, 1234, 995, 928, 755, 665 cm$^{-1}$. $^1$HNMR (CDCl$_3$) δ: 1.95 (quin, 4H), 2.26 (t, 4H), 2.40 (t, 4H), 3.35 (s, 4H), 3.89 (d, 4H), 3.96 (d, 4H), 5.13 (m, 8H), 5.75 (m, 4H), 7.25 (s, 2H).

EXAMPLE 26

Preparation of Compound No. 41 in Table 2

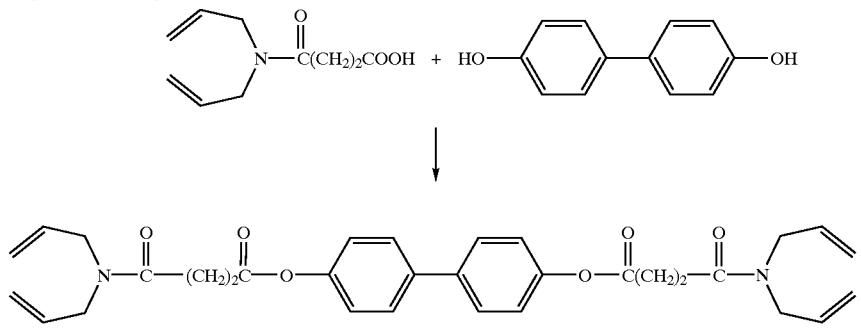

4,4'-Biphenol (5.00 g, 0.027 mol), amide A (10.64 g, 0.054 mol), dicyclohexylcarbodiimide (11.35 g, 0.055 mol) and 4-dimethylaminopyridine (0.5 g) were dissolved in dichloromethane/THF mixture (1:1) (120 cm³) and stirred at room temperature for 72 hours. The dicyclohexylurea was removed by filtration and solvents removed in vacuo to leave a yellow oil. Column chromotography using flash silica gel and ethyl acetate as the eluent gave, after removal of solvent in vacuo, a white crystalline powder which was recrystallised from acetonitrile.

Yield 10.7 g, 73%. ¹HNMR (CDCl₃) δ: 2.76 (t, 4H), 2.95 (t, 4H), 3.93 (d, 4H), 4.03 (d, 4H), 5.16 (m, 8H), 5.80 (m, 4H), 7.20 (m, 4H), 7.53 (m, 4H). Ir vmax (KBr, disc): 2935, 1761(s), 1648(s), 1499, 147?, 1444, 1416, 1370, 1228, 1200, 1146, 100?, 919, 890, 807, 556, 520 cm⁻¹.

EXAMPLE 27

Preparation of Compound No. 42 in Table 2

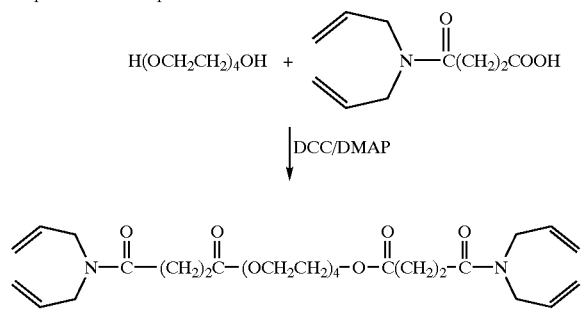

Tetraethylene glycol (5.0 g, 0.026 mol), amide above (10.25 g, 0.052 mol), dicyclohexylcarbodiimide (10.73 g, 0.052 mol) and 4-dimethylaminopyridine (0.50 g) were placed in dry dichloromethane and stirred at room temperature for 24 hours. Dicyclohexylurea was removed by filtration and solvent removed in vacuo to leave a yellow oil. Chromatography using silica gel and ethyl acetate as the eluent gave, after removal of solvent in vacuo, a pale yellow oil, 12.30 g, 87%.

Ir vmax (thin film): 3492, 3015, 2927, 1739(s), 1645(s), 1417, 1223, 1176, 995, 928, 753, 667, 557 cm⁻¹. ¹HNMR (CDCl₃) δ: 2.68 (m, A: B, 8H), 3.68 (m, 12H), 3.90 (d, 4H), 3.95 (d, 4H), 4.24 (m, 4H), 5.18 (m, 8H), 5.78 (m, 4H).

EXAMPLE 28

Preparation of Compound No. 43 in Table 2

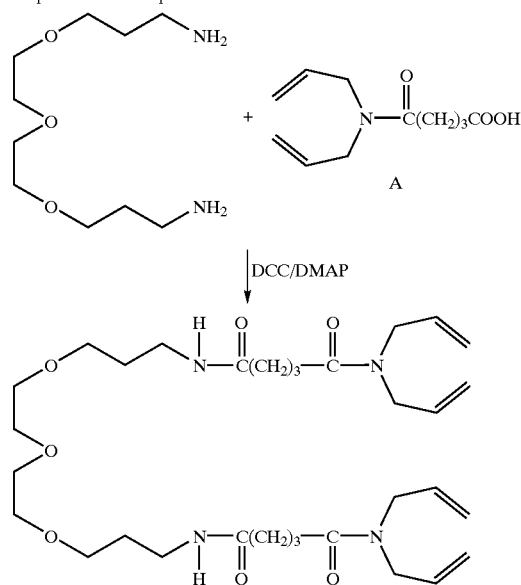

4,7,10-Trioxa-1, 13-tridecanediamine (5.0 g, 0.027 mol), amide A. (9.60 g, 0.054 mol), dicyclohexylcarbodiimide (11.14 g, 0.054 mol) and 4-dimethylaminopyridine (0.50 g) were placed in dichloromethane/THF mixture (1:1) and stirred at room temperature for 4 days. The dicyclohexylurea was removed by filtration and the solvent removed in vacuo to leave a yellow oil. Column chromatography using silica gel ethyl acetate, followed by removal of solvent, gave a clear oil, 12.41 g, 91%.

Ir vmax (thin film): 3308(s), 3086, 2937, 1659(s), 1553, 1419, 1352, 1232, 1117, 996, 928, 561 cm⁻¹. ¹HNMR (CDCl₃) δ: 1.76 (quin, 4H), 1.95 (quin, 4H), 2.22 (t, 4H), 2.40 (t, 4H), 3.32 (q, 4H), 3.55 (t, 4H), 3.66 (m, A: B 8H), 3.89 (d, 4H), 3.99 (d, 4H), 5.15 (m, 8H), 5.75 (m, 4H), 6.72 (d, 2H).

EXAMPLE 29

Preparation of Compound No. 44 in Table 2

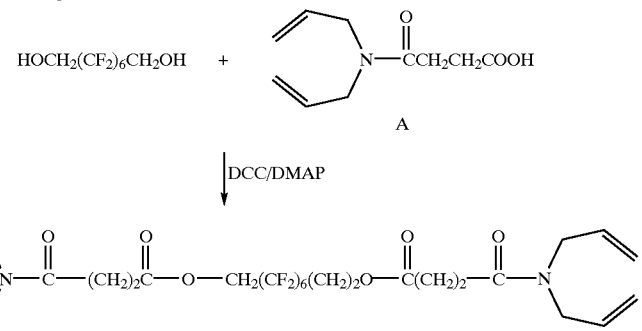

Dodecafluoro-1,8-octanediol (5.0 g, 0.0138 mol), amide A (5.42 g, 0.028 mol), dicyclohexylcarbodiimide (5.77 g, 0.028 mol) and dry dichloromethane (100 cm³) was mixed with 4-dimethylaminopyridine (0.5 g) and the mixture stirred for 72 hours. Dicyclohexylurea was removed by filtration and solvent removed to leave a clear, colourless oil. Column chromotography using silica gel/ethyl acetate and removal of solvent in vacuo gave a clear, colourless oil of one spot purity (thin layer chromotography), 7.45 g, 75%.

Ir νmax (thin film): 3091, 2937, 1769(s), 1638(s), 1539, 1417, 1368, 1200(v.s.), 993, 929, 837, 762, 667, 554 cm$^{-1}$. $^1$HNMR (CDCl$_3$) δ: 2.65 (m, 4H), 2.8 (m, 4H), 3.90 (d, 4H), 4.0 (d, 4H), 4.60 (t, 4H), 5.15 (m, 8H), 5.75 (m, 4H).

EXAMPLE 30

Preparation of Compound No. 45 in Table 2

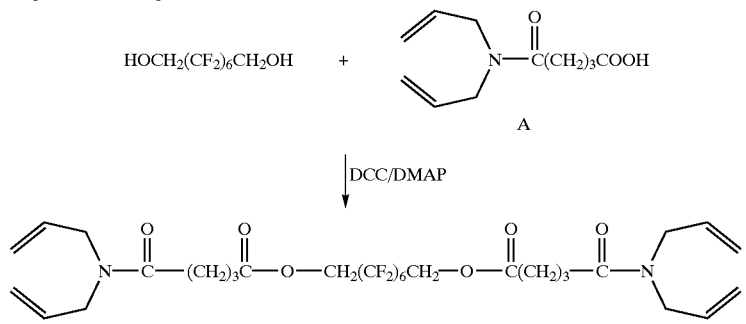

Dodecafluoro-1,8-octandiol (10.00, 0.028 mol), amide acid A (11.82 g, 0.056 mol) and dicyclohexylcarbodiimide (11.60 g, 0.056 mol) were dissolved in dry dichloromethane (200 cm³). 4-dimethylaminopyridine (0.75 g) was added and the mixture was stirred for 72 hours at room temperature. The dicyclohexylurea formed in the reaction was removed by filtration (Whatman No. 1 filter paper) and the solvent removed in vacuo to leave a clear oil. Column chromatography using flash silica gel with ethyl acetate as the eluent followed by removal of solvent in vacuo gave a clear, light yellow oil of one spot purity (Thin layer chromatography), 14.2 g, 69%.

Ir νmax (thin film) 3091, 2937, 1769(s), 1638(s), 1539, 1417, 1368, 1200(v.s.), 993, 929, 837, 762 cm$^{-1}$. $^1$HNMR (CDCl$_3$) δ: 2.65 (m, 4H), 2.85 (m, 4H), 3.95 (d, 4H), 4.00 (d, 4H), 4.65 (t, 4H), 5.15 (m, 8H), 5.75(m, 4H).

EXAMPLE 31

Preparation of Compound No. 46 in Table 2

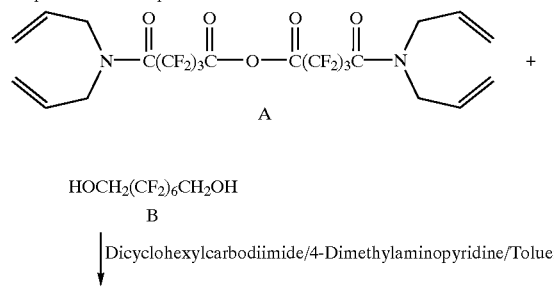

-continued

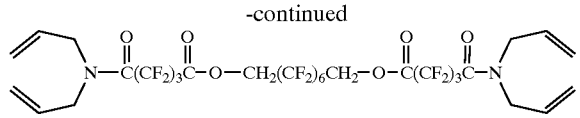

Symmetrical anhydride A (3.0 g, 0.007 mol) and 2,2,3,3,4,4,5,5,6,6,7,7-Dodcafluoro-1,8-octanediol (2.53 g (0.007 mol) (diol B), with dicyclohexylcarbodiimide (1.45 g, 0.007 mol) and 14-Dimethylaminopyridine (0.5 g) were heated together at 100° C. for 4 hours in dry toluene (80 cm³). Thin layer chromatography (ethyl acetate) showed a new spot at ~Rf 0.4 with a concomitant disappearance of the spot corresponding to the anhydride.

The reaction mixture was cooled and the Dicyclohexylurea removed by filtration (Whatman No. 1 filter paper). Solvent was removed in vacuo to leave a brown oil. The oil was dissolved in dry dichloromethane (75 cm³) and washed with 5M HCl (50 cm³) then brine (50 cm³) and dried over MgSO$_4$. Removal of solvent left a yellow oil which was purified using column chromatography (silica gel with ethyl acetate as eluent). Removal of solvent gave 4.2 g, 78% as a yellow oil.

Ir νmax (thin film) 3353, 2942, 2865, 1771(s), 1725(u), 1682(s), 1525, 1452, 1373, 1204, 1077, 933, 839, 735 cm$^{-1}$. $^1$HNMR (CDCl$_3$) δ: 4.10 (m, 8H), 4.59 (t, OCH$_2$CF$_2$ C—F splitting), 5.28 (m, 8H), 5.78 (m, 4H).

EXAMPLE 32

Preparation of Compound No. 47 in Table 2

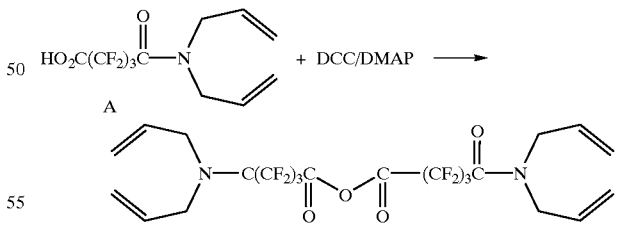

Amidoacid A (3.0 g, 0.0135 mol) was dissolved in dry dichloromethane and the dicyclohexylcarbodiimide (1.39 g, 0.0068 mol) was added in one position followed by 4-dimethylaminopyridine (0.5 g). After a few seconds the reaction mixture became turbid and was left stirring at room temperature for 1 hour. The dicyclohexylurea formed in the reaction was removed by filtration (Whatman No. 1 filter paper) and solvents removed in vacuo to leave a yellow oil.

Ir νmax (thin film): 3087, 2940, 1794(s), 1650, 1610, 1488, 1419, 1258, 1130, 994, 925 cm$^{-1}$.

EXAMPLE 33

Preparation of Compound No. 48 in Table 2

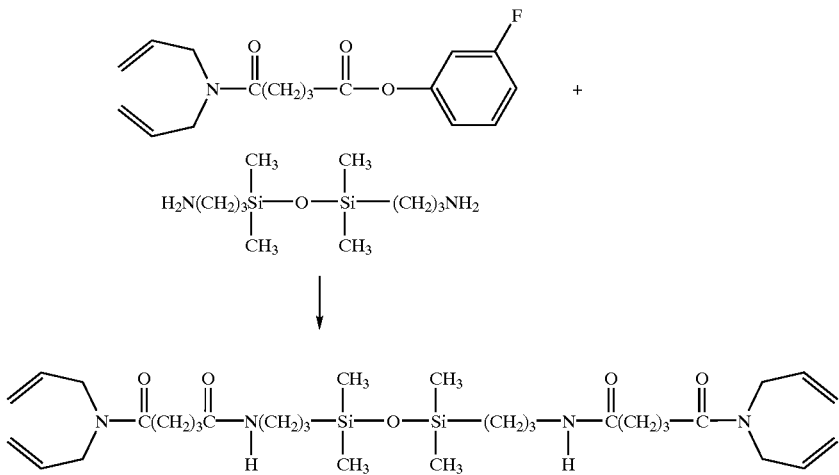

Amidoester A (5.0 g, 0.0164 mol) and 1,3-bis(aminopropyl)tetramethyl disiloxane (2.04 g, 0.0082 mol) were placed in dry toluene (75 cm$^3$) and heated to reflux. This was maintained for 3 hours. Thin layer chromatography (ethyl acetate) showed a diminution of the starting material spot and a new spot in the same vicinity of the phenol leaving group. 3M KOH solution (50 cm$^3$) was added (to remove the phenol leaving group) and the organic layer was separated and dried over MgSO$_4$. Removal of solvent in vacuo left a brown oil which was purified using silica gel column chromatography with ethyl acetate as the eluent. Removal of solvent in vacuo gave a pale yellow oil. 5.2 g, 99%.

Ir vmax (thin film): 3087, 2959, 1649(s), 1551, 1417, 1256, 1055, 925, 840, 794 cm$^{-1}$. $^1$HNMR (CDCl$_3$) δ: 0.00 (m, 12H), 0.50 (m, 4H), 1.50 (m, 4H), 1.90 (quin, 4H), 2.20 (M, 4H), 2.35 (t, 4H), 3.12 (q, 4H), 3.82 (M, 4H), 3.94 (d, 4H), 5.10 (m, 8H), 5.70 (m, 4H), 6.42 (t, 2H).

EXAMPLE 34

Preparation of Compound No. 49 in Table 2

4,4'-Diaminodicyclohexylmethane (3.45 g, 0.0164 mol) and amidoester A (10.0 g, 0.033 mol) were dissolved in toluene (100 cm3) and the combination was heated to 70–80° C. for 15 hrs. Thin layer chromatography (ethyl acetate) showed a new spot just above origin.

The solution was washed with 5M potassium carbonate solution (100 cm$^3$) 3M HCl solution (100 cm$^3$), brine (100 cm$^3$), then dried over MgSO$_4$. Removal of solvent in vacuo left a brown oil. Column chromatography using flash silica gel and ethyl acetate—methanol (4:1) as eluent gave, after removal of solvent in vacuo, a heavy yellow oil, 8.30 g, 85%.

Ir vmax (thin film): 3307(s), 3086, 2932, 2857, 1649(s), 1546, 1417, 1354, 1230, 994, 927, 753 cm$^{-1}$. $^1$HNMR (CDCl$_3$) δ: 0.95–1.26 (m, 10H), 1.80 (m, 4H), 1.85 (d, 2H), 1.95 (m, 8H), 2.15 (m, 4H), 2.45 (m, 4H), 3.70 (m, 2H), 3.85 (d, 4H), 3.95 (d, 4H), 5.20 (m, 8H), 5.80 (m, 6H).

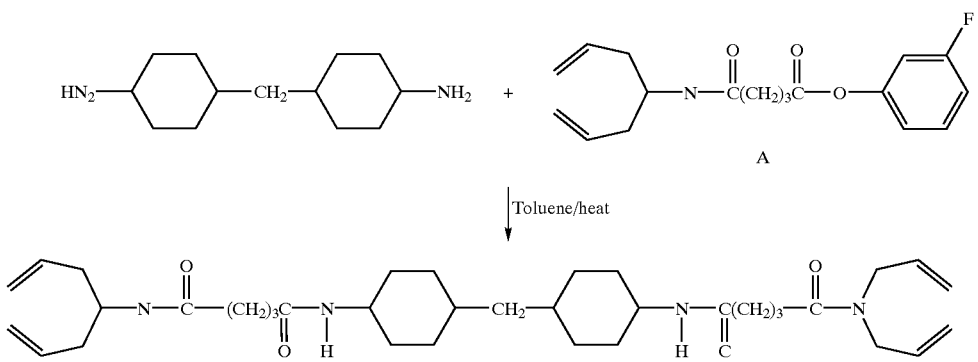

EXAMPLE 35

Preparation of Compound No. 50 in Table 2

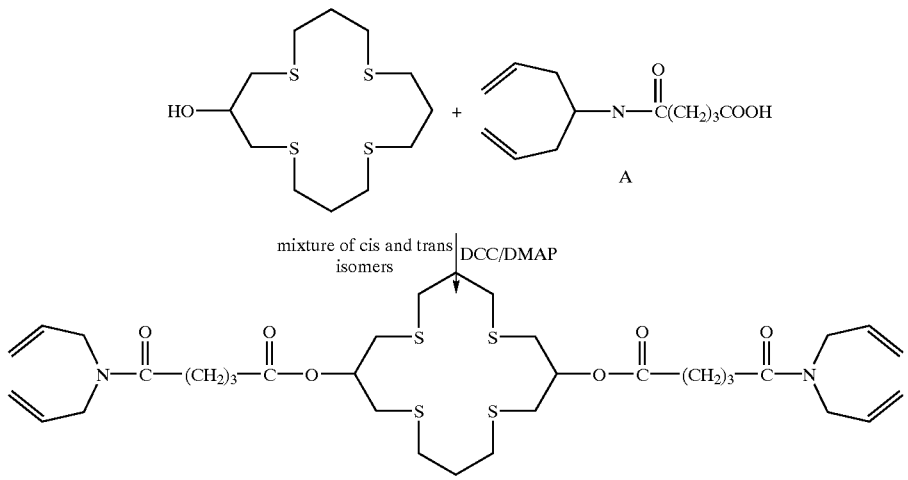

1,5,9,13-Tetrathiacyclohexadecane-3,11-diol (1.0 g, 0.00304 mol), amidoacid A (1.28 g, 0.0061 mol), dicyclohexylcarbodiimide (1.26 g, 0.0061 mol) and 4-dimethylaminopyridine (200 mg) were placed in dry toluene (50 cm$^3$) and the solution heated to 90° C. and kept at that temperature for 4 hours. Thin layer chromatography (ethyl acetate) showed two new spots (cis and trans) at ~Rf 0.5 and an absence of starting materials. The solvent was removed in vacuo to leave a clear oil which was purified using column chromotography (ethyl acetate silica gel). Removal of solvent in vacuo gave a white, clear, heavy oil, 1.40 g, 64%.

$^1$HNMR (CDCl$_3$) δ: 1.95 (septet, 8H), 2.40 (q, 8H), 2.75 (m, 12H), 2.86 (d, 2H), 2.91 (d, 2H), 3.88 (d, 4H), 3.99 (d, 4H), 5.10 (m, 10H). Ir vmax (thin film): 3297, 2934, 2861, 1736(s), 1645(s), 1530, 1417, 1230, 1153, 995, 755, 558 cm$^{-1}$.

EXAMPLE 36

Preparation of Compound No. 53 in Table 2

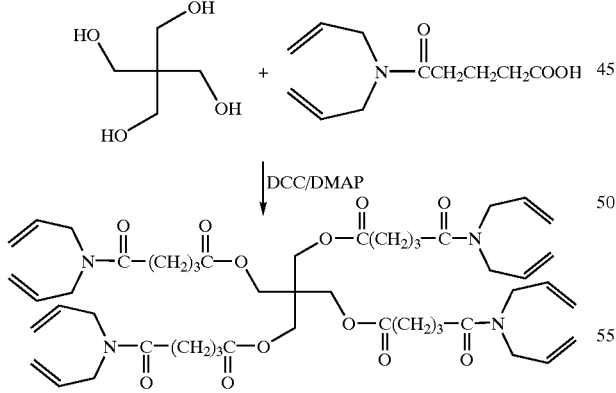

Amide A (23.21 g, 0.11 mol), pentaerythritol (3.75 g, 0.028 mol), dicyclohexylcarbodiimide (22.70 g, 0.11 mol) and 4-dimethylaminopyridine (0.50 g) were placed in THF/dichloromethane mixture (1:1) and left stirring at room temperature for 5 days. The resultant dicyclohexylurea was removed by filtration and the solvent removed in vacuo to leave a yellow oil. Column chromatography using silica gel and ethyl acetate followed by methanol gave, after removal of solvent in facuo 23.6 g, 95% of pale yellow oil.

Ir vmax (thin film): 2938, 1743(s), 1649(s), 1417, 1225, 1149, 996, 926, 559 cm$^{-1}$. $^1$HNMR (CDCl$_3$) δ: 1.95 (quin, 8H), 2.40 (quartet, 16H), 3.88 (d, 8H), 3.97 (d, 8H), 4.10 (s, 8H), 5.16 (m, 16H), 5.77 (m, 8H).

EXAMPLE 37

Preparation of Compound No. 54 in Table 2

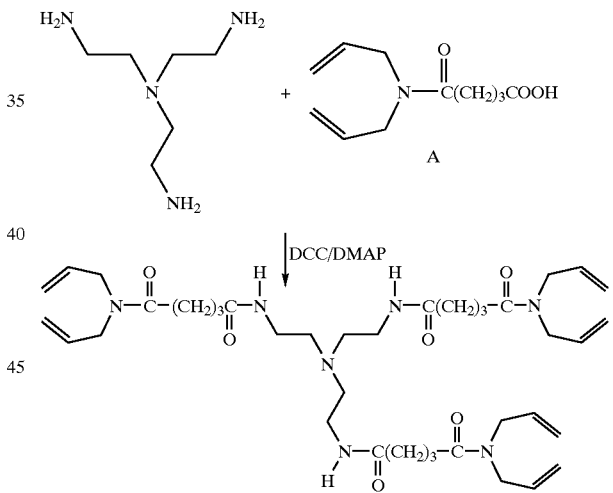

Tris(2-aminoethyl)amine (2.08 g, 0.0142 mol) and dicyclohexylcarbodiimide (8.87 g, 0.043 mol) were placed in dry dichloromethane (100 cm$^3$) and stirred at room temperature. Amide A (9.0 g, 0.043 mol) in dry dichloromethane (20 cm$^3$) was added dropwise over 30 minutes and the whole was left to stir for five days. The dicyclohexylurea was removed by filtration (Whatman No. 1 filter paper) and the solvent removed in vacuo to leave a yellow oil. The oil was purified using chromatography (ethyl acetate followed by methanol). Removal of solvent gave a pale yellow oil, 8.94 g, 87%.

Ir vmax (thin film): 3321(s), 3086, 2934, 1620, 1551, 1420, 1358, 1234, 1136, 1060, 994, 927, 756, 665, 560 cm$^{-1}$. $^1$HNMR (CDCl$_3$) δ: 1.95 (quin, 6H), 2.28 (t, 6H), 2.41 (t, 6H), 2.56 (t, 6H), 3.26 (q, 6H), 3.95 (d, 6H), 3.96 (d, 6H), 5.14 (m, 12H), 5.75 (m, 6H), 7.28 (t, 3H).

EXAMPLE 38

Preparation of Compound No. 55 in Table 2

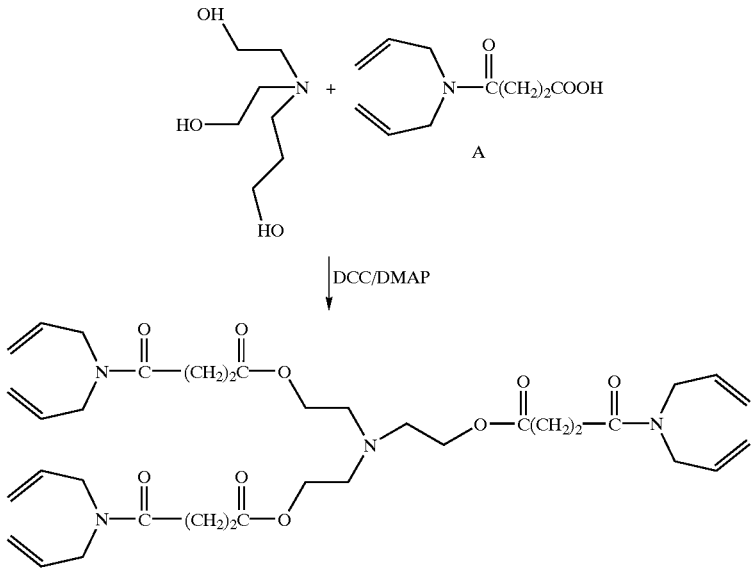

Triethanolamine (5.10 g, 0.034 mol), Amide A (20.0 g, 0.10 mol), dicyclohexylcarbodiimide (20.60 g, 0.10 mol) and 4-dimethylaminopyridine (0.5 g) were dissolved in dry dichloromethane and the solution stirred for 48 hours. The resultant dicyclohexylurea was removed by filtration and the solvent removed in vacuo to leave a yellow oil. The oil was redissolved in dichloromethane and washed with 3M HCl solution (100 ml), then brine (100 ml), then dried over $MgSO_4$. The solvent was removed in vacuo to leave an oil which was purified via column chromatography using silica gel with ethyl acetate as the eluent. Removal of solvent in vacuo left 21.4 g, 91% as a pale yellow oil.

Ir vmax (thin film) 3087, 2932, 1738, 1654, 1416, 1223, 1169, 995, 927, 755, 666, 557 $cm^{-1}$. $^1$HNMR ($CDCl_3$) δ: 2.65 (m, 12h), 2.85 (t, 6H), 3.90 (d, 6H), 3.98 (d, 6H), 4.13 (t, 6H), 5.10 (m, 12H), 5.76 (m, 6H).

EXAMPLE 39

Preparation of Compound No. 56 in Table 2

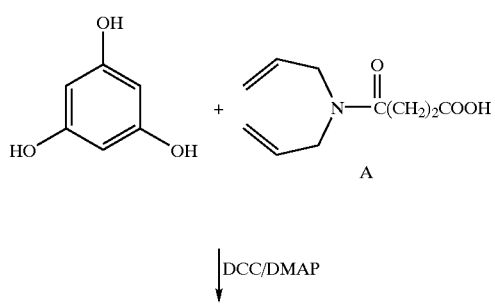

-continued

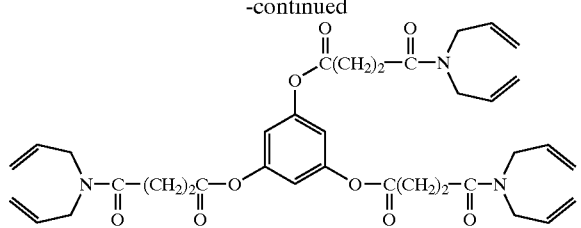

Phlorglucinol dihydrate (5.0 g, 0.031 mol), amide A (15.43 g, 0.095 mol), dicyclohexylcarbodiimide (19.60 g, 0.095 mol) and 4-dimethylaminopyridine (0.5 g) were placed in dry dichloromethane and stirred for 48 hours at room temperature. Dicyclohexylurea was removed by filtration and the solvent removed in vacuo to leave a clear oil. Column chromatography using silica gel and ethyl acetate followed by removal of solvent in vacuo gave a clear oil, 16.40 g, 76%.

Ir vmax (thin film): 3088, 3016, 2932, 1769(s), 1656(s), 1417, 1369, 1226, 1131, 997, 927, 756, 667, 556 $cm^{-1}$. $^1$HNMR ($CDCl_3$) δ: 2.72 (t, 6H), 2.88 (t, 6H), 3.91m, 6H), 4.00 (m, 6H), 5.15 (m, 12H), 5.76 (m, 6H), 6.80 (s, 3H).

EXAMPLE 40

Preparation of Compound No. 57 in Table 2

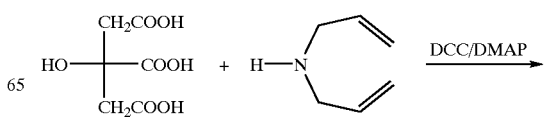

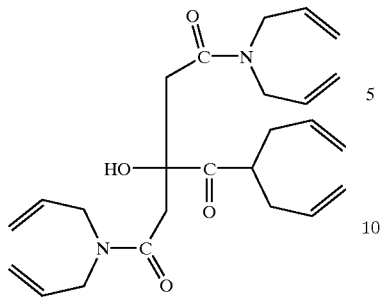

Citric acid (10.0 g, 0.048 mol) and diallylamine (14.0 g, 0.145 mol) were carefully placed in 25 cm³ THF-Dichloromethane (1:1) and stirred for 30 minutes. Dicyclohexylcarbodiimide (25 cm³) (30.0 g, 0.145 mol) was added slowly and carefully to the reaction mixture. Finally 4-dimethylaminopyridine (1.0 g) was added and the mixture was stirred at room temperature for 8 days. Thin layer chromatography (ethyl acetate) showed a major new product and several smaller ones. The dicyclohexylurea was removed by filtration (Whatman No. 1 filter paper) and the solvent removed in vacuo to leave a yellow oil. The oil was redissolved in dichloromethane (150 cm³) and washed with (i) 3M HCl solution (100 cm³), (ii) 3M Na$_2$CO$_3$ solution (100 cm³), (iii) brine (100 cm³), then dried over MgSO$_4$. Removal of solvent in vacuo left a yellow oil which was dried thoroughly to leave 12.37 g, 58% of product.

Ir vmax (thin film): 3294, 3086, 2987, 1737(w), 1637(s), 1400 1345, 1228, 1137, 995, 921, 756, 690 cm⁻¹. ¹HNMR (CDCl$_3$) δ: 2.24 (s, 4H), 3.20 (s, br, 1H), 3.8 (d, 6H), 3.99 (d, 6H), 5.20 (m, 12H), 5.78 (m, 6H).

EXAMPLE 41

Preparation of Compound No. 58 in Table 2

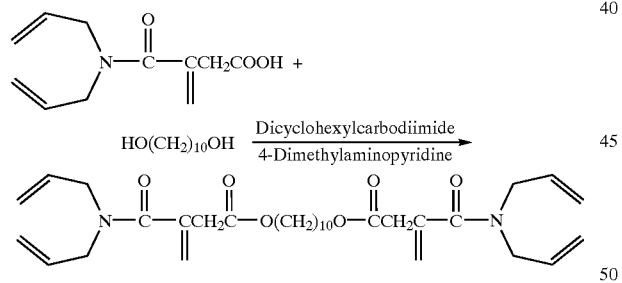

Amidoacid A (5.44 g, 0.026 mol), 1,10-decanediol (2.10 g, 0.012 mol), Dicyclohexylcarbodiimide (5.36 g, 0.026 mol) and 4-Dimethylaminopyridine (0.50 g) were stirred together in dry dichloromethane (100 cm³) at room temperature for 15 hours. The blood-red mixture was filtered to remove Dicyclohexylurea and the solvents removed in vacuo to leave a red oil. The oil was purified using column chromatography with silica gel and Dichloromethane as the eluent. Removal of solvent in vacuo left an orange coloured oil, 2,34 g, 28% (low yield due to side reactions).

Ir vmax (thin film) 3264, 3086, 2935, 2861, 2121, 1731 (s), 1650(s), 1550, 1468(s), 1222, 995, 926, 756, 665, 556 cm⁻¹. ¹HNMR (CDCl$_3$) δ: 1.10–1.40 (m, 12H), 1.60–1.70 (m, 4H), 3.40 (s, 4H), 3.90–4.35 (m, complex, 12H), 5.15 (m, 8H), 5.65 (s, 2H), 6.35.

EXAMPLE 42

Preparation of Compound No. 59 in Table 2

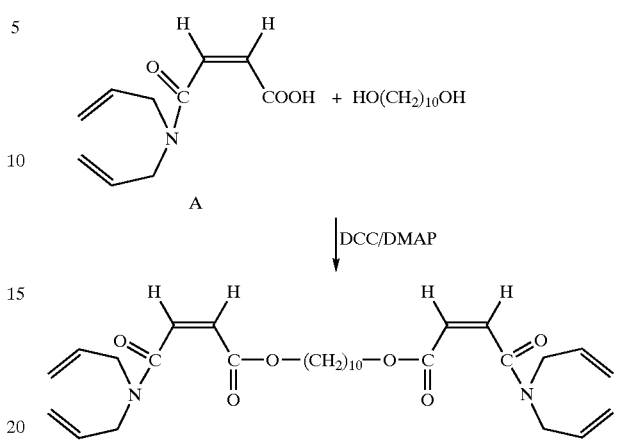

Amidoacid A (5.0 g, 0.026 mol), 1,10-decandiol (2.10 g, 0.012 mol), dicyclohexylcarbodiimide (5.36, 0.026 mol) and 4-dimethylaminopyridine (0.5 g) were placed in dry dichloromethane and the mixture was stirred for 18 hours. The dicyclohexylurea was removed by filtration (Whatman No. 1 filter paper) and the solvent removed in vacuo to leave a yellow oil. Column chromatography (silica gel) with ethyl acetate 40/60 petrol (1:1) followed by removal of solvent in vacuo gave a yellow oil, 1.90 g, 30%. Low yield due to side reactions.

Ir vmax (thin film): 3959, 3810, 3745, 3301, 2941, 2861, 2670, 2592, 2461, 2369, 2346, 2307, 2183, 1930, 1697, 1652, 1531, 1447, 1237, 993, 925, 755, 560 cm⁻¹. ¹HNMR (CDCl$_3$) δ: 1.00–2.50 (m, 14H), 3.80 (d, 4H), 3.95 (d, 4H), 4.20 (t, 4H), 5.20 (m, 8H), 5.75 (m, 8H), 7.70 (d, 2H).

EXAMPLE 43

Preparation of Compound No. 60 in Table 2

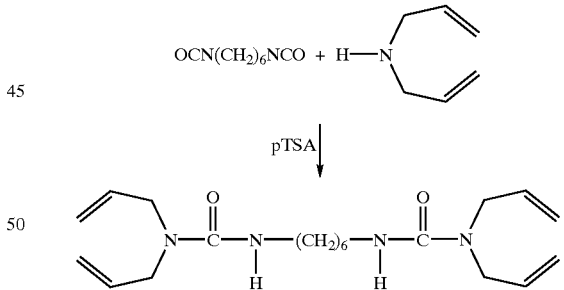

1,6-Diisocyanatohexane (10.6 g, 0.060 mol) was dissolved in dry dichloromethane (100 cm³) and the solution was cooled to ~5° C. in a salt/ice bath. p-Toluenesulphonic acid ((1.0 g) was added and the combination was stirred. Diallylamine (11.60 g, 0.120 mol) in dry dichloromethane (25 cm³) was added dropwise, slowly over 20 minutes. There was an immediate. exothermic reaction with the temperature rising to 25–35° C. with each addition of diallylamine. When addition was complete, the reaction mixture was left stirring for a further 1 h, rising to room temperature. The resultant solution was washed in (i) 3N HCl (100 cm³), 3M, K$_2$CO$_3$ solution (100 cm³) and then brine (100 cm³). The solution was dried over magnesium sulphate. Removal of solvent left a white solid. Thin layer chromatography (ethyl acetate) showed one spot only at ~Rf 0.25. 19.7 g, 92%.

¹HNMR (CDCl₃) δ: 1.30 (quin, 4H), 1.45 (quin, 4H), 3.20 (quar, 4H), 3.85 (d, 8H), 4.55 (t, 2H), 5.18 (m, 8H), 5.75 (m, 4H). Ir νmax (KCl, disc): 3362(s), 3088, 3019, 2985, 2944, 1624(s), 1536(s), 1477, 1406, 1380, 1256, 1218, 1110, 1064, 995, 966, 923, 903, 765, 542 cm⁻¹.

EXAMPLE 44

Preparation of Compound No. 61 in Table 2

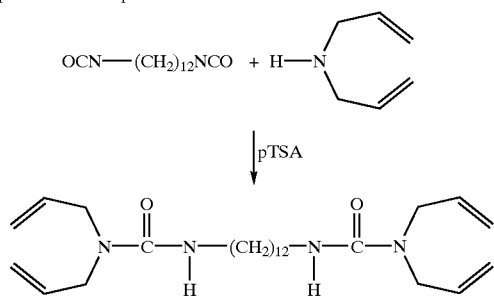

1,12-Diisocyanotododecane (5.0 g, 0.040 mol) was dissolved in dry dichloromethane (70 cm³) and the solution was cooled in a salt/ice bath. p-Toluene sulphonic acid (100 mg) was added and the combination was stirred. Diallylamine (4.86 g, 0.10 mol) in dry dichloromethane (15 cm³) was added slowly over ~15 min. A rise in temperature was observed as the addition proceeded (25–30° C.). When addition was complete, the reaction mixture was left stirring for a further 1 h, rising to room temperature. The resultant solution was washed in (a) 3M HCl (120 cm³), (2) 3M K₂CO₃ solution (100 cm³) and brine (100 cm³). The solution was dried over MgSO₄. Removal of solvent left a clear oil which solidified on standing. Thin layer chromatography (ethyl acetate) showed one spot at ~Rf 0.25. The solid was suspended in 40/60 petrol and stirred for 30 min then recovered by filtration (No. 1 Sinter) and dried in vacuo. Yield 7.8 g, 94%.

Mpt 80–82° C. ¹HNMR (CDCl₃) δ: 1.25 (d, 16H), 1.45 (t, 4H), 3.20 (q, 4H), 3.85(d, 8H), 4.44 (t, 2H), 5.20 (m, 8H), 5.80 (m, 4H). Ir νmax (thin film) 3352(s), 3087, 2928, 2856, 1620(s), 1532(s), 1475, 1402, 1371, 1264, 1238, 1096, 1061, 995, 920, 765, 725, 674 cm⁻¹.

EXAMPLE 45

Preparation of Compound No. 62 in Table 2

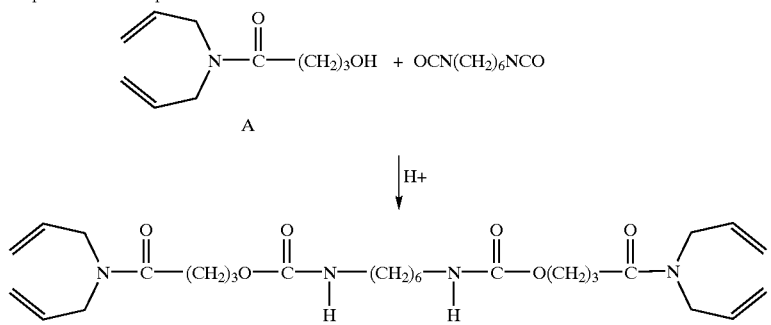

Amidoalcohol A (9.0 g, 0.049 mol) and 1,6-diisocyanatohexane (4.14 g, 0.025 mol) were placed in toluene (75 cm³) and stirred at room temperature. p-Toluenesulphonic acid (100 mg) was added and the combination was left stirring at room temperature for 72 hours. Thin layer chromatography (ethyl acetate) showed a new compound at ~Rf 0.25. The solvent was removed in vacuo and the residual brown oil dissolved in dichloromethane. The resultant solution was washed in brine (120 cm³) then dried over MgSO₄. Removal of solvent in vacuo left a brown oil which was purified using column chromatography (flash silica with ethyl acetate as eluent). Removal of solvent in vacuo gave a clear, colourless, heavy oil. 12.0 g, 92%.

Ir νmax (thin film): 3336(s), 3087(w), 2939, 1721(s), 1640(s), 1542(s), 1471, 1417, 1256, 1143, 1044, 995, 927, 756, 664 cm⁻¹. ¹HNMR (CDCl₃) δ: 1.32 (m, 4H), 1.59 (m, 4H), 1.90 (m, 4H), 2.35 (t, 4H), 3.20 (q, 4H), 3.85 (d, 4H), 3.95 (d, 4H), 4.10 (t, 4H), 4.90 (s, br, 2H), 5.19 (m, 8H), 5.80 (m, 4H).

EXAMPLE 46

Preparation of Compound No. 63 in Table 2

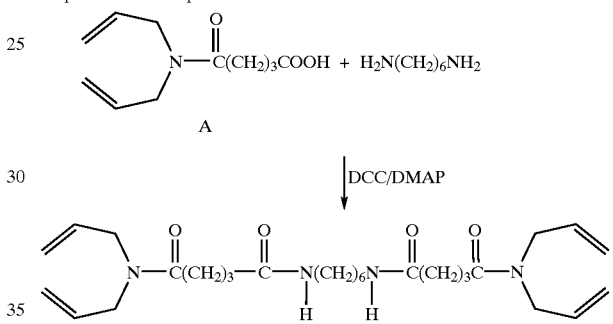

To Amidoacid A (20.0 g, 0.094 mol) was added 25 cm³ of dry dichloromethane and the solution was added slowly dropwise to a mixture of 1,6-diaminohexane (5.34 g, 0.046 mol), dicyclohexylcarbodiimide (19.80 g, 0.096 mol) and 4-Dimethylaminopyridine (0.50 g) in dry dichloromethane. (200 cm³) with stirring. The mixture was left stirring at room temperature for 18 hours.

Dicyclohexylurea was removed by filtration (Whatman No. 1 filter paper). Removal of solvent in vacuo left a yellow oil. The oil was dissolved in dichloromethane (100 cm³) and the solution washed in 3M Na₂CO₃ (100 cm³), 5M HCl (100 cm³) then water and then dried over MgSO₄. Removal of solvent in vacuo, followed by column chromatography (silica gel, ethyl acetate methane 4:1) gave, after removal of solvent in vacuo, a yellow oil, 12.5 g, 54%.

Ir vmax 3300(s), 3085, 2935, 2860, 1660, 1637(s), 1556, 1416, 1347, 1232, 1158, 993, 925, 691 cm$^{-1}$. $^1$HNMR (CDCl$_3$) δ: 1.36 (quin, 4H), 1.57 (m, 4H), 2.0 (t, 4H), 2.23 (t, 4H), 2.40 (t, 4H), 3.70 (m, 4H), 3.90 (d, 4H), 4.0 (d, 4H), 5.25 (m, 8H), 5.75 (m, 4H), 6.0 (d, 2H).

EXAMPLE 47

Preparation of Compound No. 51 in Table 2

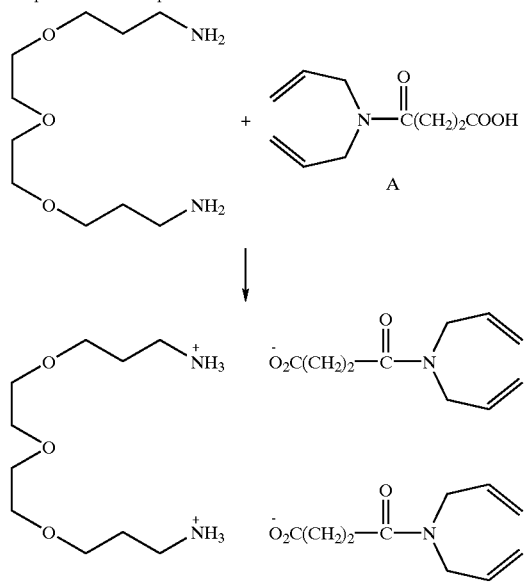

4,7,10-Trioxa-1,13-tridecanediamine (5.0 g, 0.0227 mol) and amide A (8.94 g, 0.045 mol) were dissolved in dry dichloromethane (100 cm$^3$) and stirred at room temperature for 1 hour. The solvent was removed in vacuo to leave a pale yellow oil which was not further purified since both starting materials were 98–100% pure. Yield 13.94 g, 100%.

$^1$HNMR (CDCl$_3$) δ: 1.93 (t, 4H), 2.45 (t, 4H), 2.60 (t, 4H), 3.00 (t, 4H), 3.60 (m, 12H, —CH$_2$ NH$_3$), 3.95 (m, 8H), 5.17 (m, 8H), 5.77 (m, 4H), 7.60 (s, br, 6H). Ir vmax (thin film): 2876(s), 1647(s), 1412, 1243, 1117, 997, 929, 870, 558 cm$^{-1}$.

EXAMPLE 48

Preparation of Polymer Composite

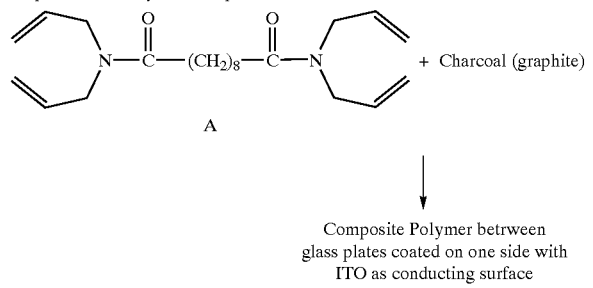

Charcoal (0.025 g, 5% (w/w)) and Irgacure (25 mg) were mixed into Monomer A (0.5 g) and the mixture heated to ~110° C. and stirred to ensure complete mixing. The mixture was then placed on a 10.5×7.5 cm indium tin oxide (ITO) coated glass plate, leaving a margin 2 cm wide at one end. A similar glass plate with ITO coating was placed over the mixture, and the two plates were squeezed together with a stagger of ~2 cm$^3$ at each end. The film was then exposed to a Philips UVA. (75 w) sunlamp for one hour. A similar cell was used using 30% w/w charcoal and polymerised in a similar manner.

Conductivity: 5% w/w charcoal Low 30% w/w/charcoal 5×10$^6$ ohms resistance

EXAMPLE 49

Preparation of Polymer Composite

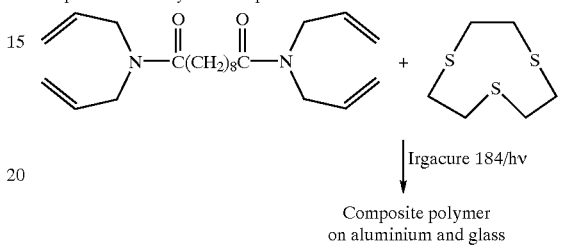

Monomer A (1.0 g, 0.0028 mol) and 1,4,7-trithiacyclononane (100 mg, 0.00056 mol, 20 mol %) were mixed and dissolved into each other. The Irgacure 184 (50 mg, 2.5% w/w) was added and the whole was heated and occasionally stirred at 115° C. for 15 minutes. Half of the resultant clear solution was placed on a plate glass and spread over an area of 3×7 cm to give a monomer film of 1 mm thickness. This was exposed to a Philips UVA (75 w) sunlamp for 90 minutes. The resultant polymer coating was washed in dry dichloromethane (25 cm$^3$) to remove surface stickiness.

The procedure was repeated exactly using the other half of the clear solution, but this time the monomer film was placed on a sheet of aluminium foil.

EXAMPLE 50

Preparation of Polymer Composite

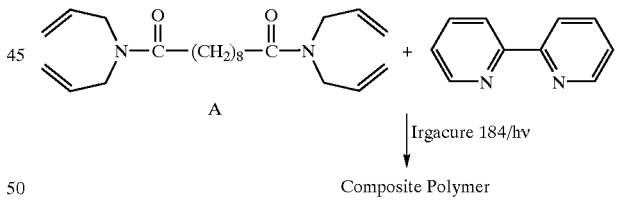

Monomer A (1.0 g, 0.0028 mol), 2,2-bipyridine (0.0875 g, 0.00056 mol, 20 mol %) and Irgacure 184 (50 mg) were heated together at 115° C. and stirred occasionally to form a clear solution. Half of the solution was spread on a plate glass plate to cover an area 5×3 cm. The monomer was warmed to form a monomer coating of even thickness. The coating was exposed to a Philips UVA (75 w) sunlamp for 90 minutes. The resultant polymer was washed with dry dichloromethane (25 cm$^3$) and dried in the hot air oven at 115° C.

The procedure was repeated exactly using the half of the clear monomer solution but this time using aluminium foil. In each case a polymer coating with a wrinkled surface was formed.

EXAMPLE 51

Preparation of Polymer Composite

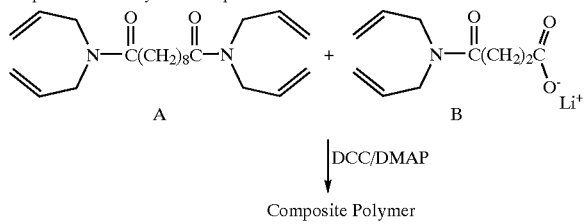

Monomer A (0.5 g) and amido lithium salt B (0.2 g), which is an insoluble solid in most organic salts, were heated together to form a homogeneous mixture. The Irgacure (35 mg) was added and the mixture heated again to ensure complete mixing. The mixture was then spread on a plate glass plate to cover an area 7×4 cm and the monomer film was warmed to form an even surface. The monomer mixture was then exposed to a Philips UVA (75 w) sunlamp for 2 hours. The polymer film was heated in the oven at 115° C. for 3 days to form a hard, brittle coating. The polymer was then removed from the plate as brittle flakes (scalpel) and dried.

Ir νmax (K Br disc): 2980, 2922, 1645(s), 1581, 1422, 1350, 1280, 1140, 912, 808 cm$^{-1}$.

EXAMPLE 52

Preparation of Polymer Composite

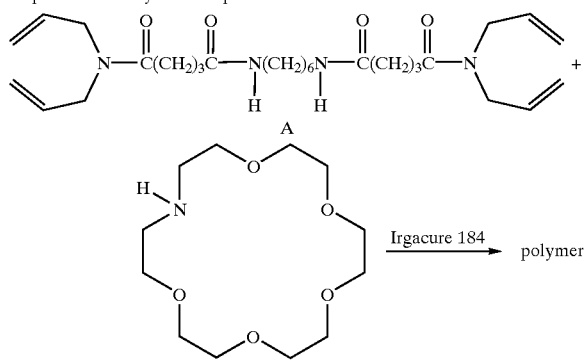

Nylon monomer A (0.50 g, 0.001 mol), 1-Aza-18-crown-6 (13.15 mg, 5×10$^{-5}$ mol, 5 mol %), Irgacure 184 (5% w/w relative to monomer) were dissolved in dry dichloromethane (3 cm$^3$) and the solution spread on a glass plate to cover an area 5×5 cm. The solvent was allowed to evaporate off to leave a clear homogeneous film. The film was irradiated with a Philips UVA (75 w) sunlamp for 1 hour. The resultant cross-linked polymer film was removed in strips (scalpel) and washed in dry dichloromethane.

EXAMPLE 53

Preparation of Polymer Composite

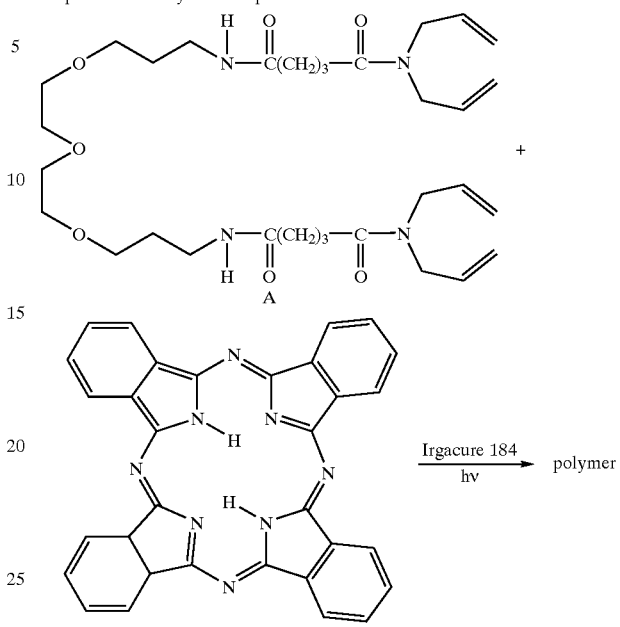

Monomer A (0.5 g, 8.2×10$^{-4}$ mol), phthalocyanine (21 mg, 5 mol %) and Irgacure 184 (25 mg, 5% w/w) were dissolved in dry dichloromethane (4 cm$^3$) to form a green/blue solution. The solution was spread on a glass plate to cover an area ~6×6 cm and the solvent was allowed to evaporate off in air. The residual monomer film was irradiated with a Philips UVA (75 w) sunlamp for 1 hour. The resultant polymer composite film was washed with dry dichloromethane to remove surface stickiness and allowed to dry in air. The polymer was then removed as strips (scalpel) and placed in a hot air oven at 115° C. for 1 hour to leave hardened, blue-green polymer strips.

EXAMPLE 58

Preparation of Polymer Composite

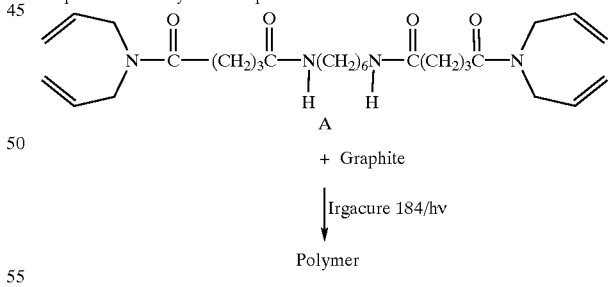

Irgacure 184 (5% w/w relative to monomer) and Nylon monomer A (0.50 g, 0.001 mol) were dissolved in dry dichloromethane (3 cm$^3$). The graphite (3.0 mg, 0.00025 mol, 25 mol %) was added and thoroughly mixed then the mixture was spread evenly on a glass plate to form a film 5×5 cm. The solvent was allowed to evaporate off in air and the film irradiated with a Philips UVA sunlamp (75 w) for 1 hour. The resultant cross-linked polymer was removed in strips and washed in dry dichloromethane then allowed to dry in air.

EXAMPLE 55

Preparation of Polymer Composite

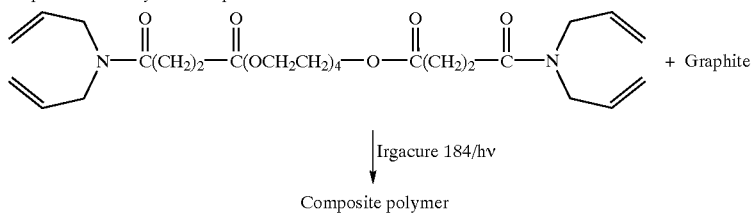

Monomer A (0.5 g, 9×10–4 mol) was dissolved in dry dichloromethane and the graphite (1.1 mg, 10 mol %)was mixed in as evenly as possible. The mixture was spread on a plate glass plate to cover an area 6×6 cm and the dichloromethane was allowed to evaporate off in air. The residual monomer composite film was irradiated with a Philips UVA sunlamp (75 w) for 1 hour. The resultant polymer composite film was washed in dry dichloromethane to remove surface stickiness and dried. it was then removed as strips (scalpel) 1 cm wide and the strips were heated in a hot air oven at 115° C. for 1 hour to leave flexible strips of composite polymer.

EXAMPLE 56

Preparation of Polymer Composite

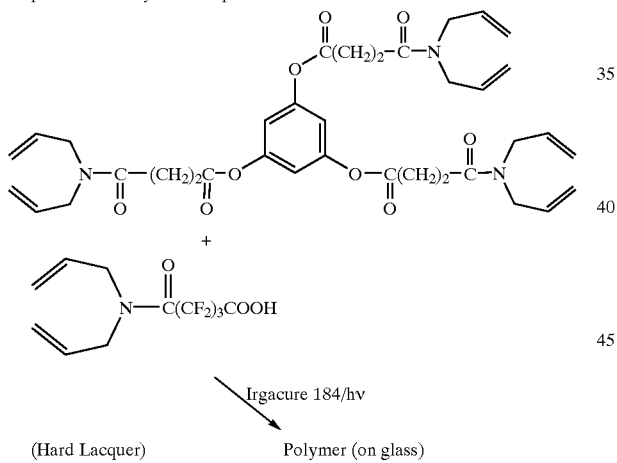

Monomers A (0.5 g) and B (0.025 g) were dissolved with the Irgacure 184 (25 mg) in dry dichloromethane (2 cm$^3$) and the solution spread over an area 3×7 cm on a plate glass plate. The solvent was allowed to evaporate to leave a thin monomer film which was irradiated with a Philips UVA (75 w) sunlamp for 1 hour. The resultant hard polymer film was washed with dry dichloromethane (20 cm$^3$) to remove surface stickiness and allowed to dry in air.

What is claimed is:

1. A compound which is polymerizable under the influence of radiation or an electron beam and is of formula (I)

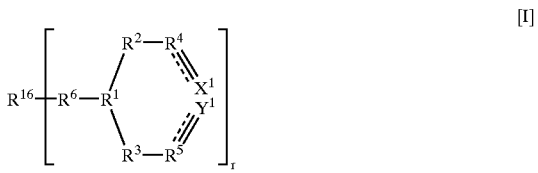

where $R^1$ is CH and $R^6$ is a bond or —C(O)— or —OC (O)— or —S(O)2, or $R^1$ and $R^6$ together form an electron withdrawing group wherein $R^1$ is $N^+R^{12}(Z^{m-})_{1/m}$, $S(O)_pR^{13}$, B or $P(O)_qR^{14}$ where $R^{12}$, $R^{13}$ and $R^{14}$ are independently selected from hydrogen or hydrocarbyl, Z is an anion of valency m, p is 0, 1 or 2, and q is 0, 1, 2 or 3 and $R^6$ is a bond;

$R^1$ is a nitrogen atom and $R^6$ is a carbonyl group;

$R^2$ and $R^3$ are independently selected from $(CR^7R^8)_n$, or a group $CR^9R^{10}$, —$(CR^7R^8CR^9R^{10})$— or —$(CR^9R^{10}CR^7R^8)$— where n is 0,1 or 2, $R^7$ and $R^8$ are independently selected from hydrogen or alkyl, and either one of $R^9$ or $R^{10}$ is hydrogen and the other is an electron withdrawing group $COCH_2CN$ or $COCH_3$, or $R^9$ and $R^{10}$ together form an oxo electron withdrawing group, and $R^4$ and $R^5$ are independently selected from CH or $CR^{11}$ where $R^{11}$ is an electron withdrawing group $COCH_3$;

the dotted lines indicate the presence or absence of a bond, and $X^1$ is a group $CX^2X^3$ where the dotted line bond to which it is attached is absent and a group $CX^2$ where the dotted line bond to which it is attached is present, $Y^1$ is a group $CY^2Y^3$ where the dotted line bond to which it is attached is absent and a group $CY^2$ where the dotted line bond to which it is attached is present, and $X^2$, $X^3$, $Y^2$ and $Y^3$ are independently selected from hydrogen and fluorine;

$R^{16}$ is a bridging group of valency r and r is an integer of 2 or more, subject to the following provisos:
(i) that where $R^1$ is CH and $R^6$ is a bond at least one of
(a) $R^2$ and $R^3$ or (d) $R^4$ and $R^5$ includes an electron withdrawing group;
(ii) that where $R^2$ and $R^3$ are both $CH_2$, $R^4$ and $R^5$ are both CH, and $R^1$ and $R^6$ together form an electron withdrawing group in which $R^1$ is a group of formula $N^+R^{12}(Z^{m-})_{1/m}$ where Z is an anion of valency m, where $R^{12}$ is selected from hydrogen or hydrocarbyl and $R^6$ is a bond, then either r is other than 2 or $R^{16}$ is other than a group $(CH_2)_x$ where x is an integer of from 2 to 10, or $R^{16}$ is other than a group

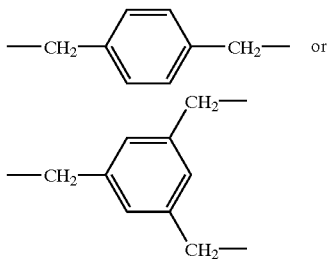

(iii) that where $R^2$ and $R^3$ are both $CH_2$, $R^4$ and $R^5$ are both CH, and $R^1$ and $R^6$ together form an electron withdrawing group in which $R^1$ is a nitrogen atom and $R^6$ is a carbonyl group, then either r is other than 2 or $R^{16}$ is other than a group or —$NHCH_2CH_2OC(O)OCH_2CH_2NH$— or —$CH_2CHR^p$— where $R^p$ is chlorine or bromine; or (iv) that where $R^2$ and $R^3$ are both $CH_2$, $R^4$ and $R^5$ are both CH, and $R^1$ and $R^6$ together form an electron withdrawing group in which $R^1$ is a group CH and $R^6$ is a group —OC(O)— where the O atom is directly bonded to the group $R^1$, then either r is other than 2 or $R^{16}$ is other than —CH=CH—.

2. A compound according to claim 1 of formula (IA)

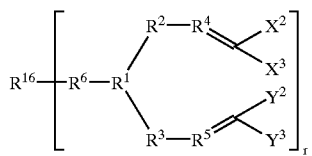 [A]

where $R^1$, $R^2$, $R^3$, $R^4$, $R^5$, $R^6$, $R^{16}$, $X^2$, $X^3$, $Y^2$ and $Y^3$ are as defined in claim 1.

3. A compound according to claim 1 wherein $R^1$ and $R^6$ form an electron withdrawing group.

4. A compound according to claim 3 wherein in the compound of formula (I), $R^2$ and $R^3$ are groups $(CR^7R^8)_n$ where $R^7$, $R^8$ and n are as defined in claim 1 and $R^4$ and $R^5$ are CH groups.

5. A compound according to claim 1 where $R^1$ is a $N^+R^{12}(Z^{m-})_{1/m}$ group where $R^{12}$, Z and m are as defined in claim 1.

6. A compound according to claim 5 where Z is halogen.

7. A compound according to claim 5 or 6 where $R^{12}$ is alkyl.

8. A compound according to claim 1 or 2 where $R^2$ and $R^3$ are electron withdrawing groups.

9. A compound according to claim 8 where at least one of $R^2$ or $R^3$ include electron withdrawing groups $R^9$ and $R^{10}$.

10. A compound according to claim 1 where r is an integer of from 2 to 6.

11. A compound according to claim 10 where r is an integer of from 2 to 4.

12. A compound according to claim 1 where $R^{16}$ comprises a straight or branched chain alkyl groups, optionally substituted or interposed with functional groups; or siloxane groups.

13. A compound according to claim 1 where r is 2 and $R^{16}$ is a group of sub-formula (II)

 (II)

where a and b are independently selected from 0, 1 or 2, $Z^1$, $Z^2$ and $Z^3$ are independently selected from a bond, an optionally substituted linear or branched alkyl or alkene chain wherein optionally one or more non-adjacent carbon atoms are replaced with a heteroatom or an amide group, $Q^1$ and $Q^2$ are independently selected from an optionally substituted carbocylic or heterocyclic ring which optionally contains bridging alkyl groups;

a and b are independently selected from 0, 1 or 2.

14. A method for preparing a compound according to claim 1 comprising reacting a compound of formula (X)

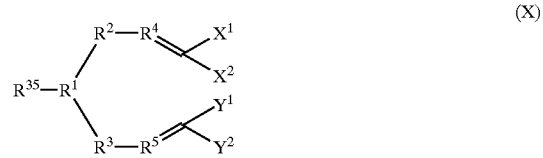 (X)

where $X^1$, $X^2$, $Y^1$, $Y^2$, $R^1$, $R^2$, $R^3$, $R^4$ and $R^5$ are as defined in claim 1, and $R^{35}$ is hydrogen or hydroxy, with a compound of formula (XI)

 (XI)

where $R^6$, $R^{16}$ and r is as defined in claim 1 and $Z^4$ is a leaving group.

15. A method according to claim 14 wherein the polymerization is controlled by the presence of a chain terminator.

16. A method according to claim 15 where the chain terminator comprises a compound of formula (XII)

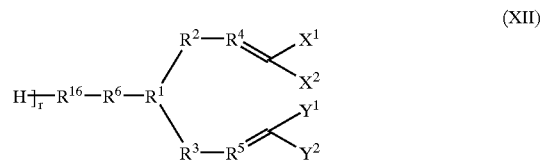 (XII)

where $X^1$, $X^2$, $Y^1$, $Y^2$, $R^1$, $R^2$, $R^3$, $R^4$, $R^5$, $R^6$, $R^{16}$ and r are as defined in claim 1.

17. A method for producing a polymeric material comprising polymerizing a compound of formula (I) as defined in claim 1 under the influence of radiation or an electron beam.

18. A method for producing a polymer which comprises subjecting a compound of formula (IB)

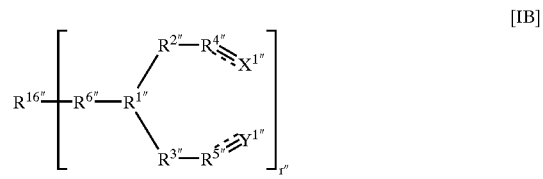 [IB]

where $R^{1''}$ is CH and $R^{6''}$ is a bond or —C(O)— or —OC(O)— or —S(O)$_2$, or $R^{1''}$ and $R^{6''}$ together form an electron withdrawing group wherein $R^{1''}$ is $N^+R^{12}(Z^{m-})_{1/m}$, $S(O)_pR^{13}$, B or $P(O)_qR^{14}$ where $R^{12}$, $R^{13}$ and $R^{14}$ are independently selected from hydrogen or hydrocarbyl, Z is a anion of valency m, p is 0, 1 or 2, and q is 0, 1, 2 or 3 and $R^{6''}$ is a bond;

$R^{1"}$ is a nitrogen atom and $R^{6"}$ is a carbonyl group;

$R^{2"}$ and $R^{3"}$ are independently selected from $(CR^{7"}R^{8"})_{n"}$, or a group $CR^{9"}R^{10"}$, $-(CR^{7"}R^{8"}CR^{9"}R^{10"})-$ or $-(CR^{9"}R^{10"}CR^{7"}R^{8"})-$ where n" is 0, 1 or 2, $R^{7"}$ and $R^{8"}$ are independently selected from hydrogen or alkyl, and either one of $R^{9"}$ or $R^{10"}$ is hydrogen and the other is an electron withdrawing group $COCH_2CN$ or $COCH_3$, or $R^{9"}$ and $R^{10"}$ together form an oxo electron withdrawing group, and $R^{4"}$ and $R^{5"}$ are independently selected from CH or $CR^{11"}$ where $R^{11"}$ is an electron withdrawing group $COCH_3$;

$X^{1"}$ and $Y^{1"}$ are groups as defined for $X^1$ and $Y^1$ respectively in relation to formula (I);

$R^{16"}$ is a bridging group of valency r" and r" is an integer of 2 or more, provided that at least one of (a) $R^{1"}$ and $R^{6"}$ or (b) $R^{2"}$ and $R^{3"}$ or (c) $R^{4"}$ and $R^{5"}$ includes an electron withdrawing group, to radiation to cause the compound of formula (Ib) to polymerize.

19. A method according to claim 10 or 18 wherein the compound of formula (I) or (IB) is polymerized with a different monomeric unit to form a copolymer.

20. A method according to claim 17 or 18 wherein the compound of formula (I) or (IB) is polymerized with a different chemical entity unit to form a polymer composite.

21. A method according to claim 17 wherein the radiation is ultraviolet radiation.

22. A method according to claim 21 which is effected in the presence of a photoinitiator.

23. A method according to claim 17 wherein the compound of formula (I) is a curable under the influence of an electron beam and polymerization is effected by subjecting the compound to such a beam.

24. A method according to claim 17 wherein the compound of formula (I) is curable in the presence of a chemical initiator and polymerization is effected by contacting the compound to such an initiator.

25. A polymeric compound of formula (XIII)

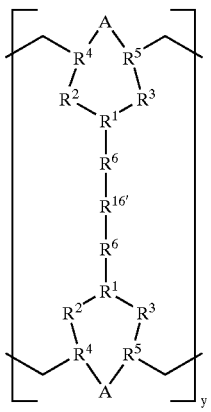

(XIII)

where A is a bond or $CH_2$, $R^1$, $R^2$, $R^3$, $R^4$, $R^5$, $R^6$ as given by formula (I) in claim 1, $R^{16'}$ is a group of formula $R^{16}$ as defined in formula (I) which may be substituted by further groups of sub formula (XIV)

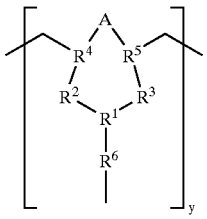

(XIV)

and y is an integer in excess of 1, and A is as defined above.

26. A polymer in accordance with claim 25 where y is an integer in excess of 5.

27. A polymer in accordance with claim 25 where y is an integer in the range from 5 to 30.

28. A method of forming a polymer coating on an article, which method comprises applying to the article a compound of formula (IB) as defined in claim 18 allowing said compound to polymerize in situ.

29. A coated article produced by the process of claim 28.

* * * * *